US012570989B2

(12) United States Patent
Xue et al.

(10) Patent No.: US 12,570,989 B2
(45) Date of Patent: \*Mar. 10, 2026

(54) PROMOTER AND USE THEREOF

(71) Applicant: Azenta US, Inc., Burlington, MA (US)

(72) Inventors: Gaoxu Xue, Suzhou (CN); Tianming Qi, Suzhou (CN); Aihua Feng, Suzhou (CN); Zhengli Xie, Suzhou (CN); Yankai Jia, Suzhou (CN); Xin Wu, Suzhou (CN); Zhongping Sun, Suzhou (CN); Guojuan Liao, Suzhou (CN)

(73) Assignee: AZENTA US, INC., Burlington, MA (US)

( \* ) Notice: Subject to any disclaimer, the term of this patent is extended or adjusted under 35 U.S.C. 154(b) by 434 days.

This patent is subject to a terminal disclaimer.

(21) Appl. No.: 16/914,266

(22) Filed: Jun. 26, 2020

(65) Prior Publication Data

US 2021/0032636 A1     Feb. 4, 2021

Related U.S. Application Data

(63) Continuation-in-part of application No. PCT/CN2018/122309, filed on Dec. 20, 2018.

(30) Foreign Application Priority Data

Dec. 29, 2017     (CN) .......................... 201711490227.9

(51) Int. Cl.
| | |
|---|---|
| *C12N 15/66* | (2006.01) |
| *C12N 9/38* | (2006.01) |
| *C12N 15/70* | (2006.01) |
| *C12N 15/72* | (2006.01) |

(52) U.S. Cl.
CPC ........... *C12N 15/66* (2013.01); *C12N 9/2471* (2013.01); *C12N 15/70* (2013.01); *C12N 15/72* (2013.01); *C12Y 302/01023* (2013.01); *C12N 2800/22* (2013.01); *C12N 2830/55* (2013.01)

(58) Field of Classification Search
CPC ...... C12N 15/66; C12N 9/2471; C12N 15/70; C12N 15/72; C12N 2800/22; C12N 2830/55; C12Y 302/01023; C12P 21/00
See application file for complete search history.

(56) References Cited

U.S. PATENT DOCUMENTS

| | | | |
|---|---|---|---|
| 5,652,095 A | 7/1997 | Taniguchi et al. | |
| 5,691,140 A | * 11/1997 | Noren .................... | C12N 15/73 |
| | | | 435/5 |
| 6,509,185 B1 | 1/2003 | Valle et al. | |
| 6,818,611 B1 | 11/2004 | Altman | |
| 6,911,322 B2 | 6/2005 | Valle et al. | |
| 7,122,516 B2 | 10/2006 | Altman | |
| 7,132,527 B2 | * 11/2006 | Payne .................... | C12P 7/18 |
| | | | 435/320.1 |
| 7,199,233 B1 | 4/2007 | Jensen et al. | |
| 2003/0148461 A1 | 8/2003 | Valle et al. | |
| 2003/0215907 A1 | 11/2003 | Samuelson et al. | |
| 2004/0115642 A1 | 6/2004 | Fu | |
| 2004/0235091 A1 | 11/2004 | Altman | |
| 2008/0058245 A1 | 3/2008 | Johnson et al. | |
| 2015/0067922 A1 | 3/2015 | Yang et al. | |
| 2016/0272965 A1 | 9/2016 | Zhang et al. | |
| 2017/0009221 A1 | 1/2017 | Arikawa et al. | |
| 2018/0298377 A1 | 10/2018 | Levy et al. | |
| 2021/0040488 A1 | 2/2021 | Xue et al. | |

FOREIGN PATENT DOCUMENTS

| | | |
|---|---|---|
| CN | 1190993 A | 8/1998 |
| CN | 1233287 A | 10/1999 |
| CN | 1425071 A | 6/2003 |
| CN | 104513830 A | 4/2015 |
| CN | 105400809 A | 3/2016 |
| CN | 105886616 A | 8/2016 |
| CN | 105907632 A | 8/2016 |
| CN | 106845151 A | 6/2017 |
| CN | 106939310 A | 7/2017 |
| CN | 107058316 A | 8/2017 |
| CN | 107090466 A | 8/2017 |
| CN | 107365793 A | 11/2017 |
| CN | 108060168 A | 5/2018 |
| CN | 108118058 A | 6/2018 |
| CN | 108118059 A | 6/2018 |
| CN | 108130338 A | 6/2018 |
| CN | 108165551 A | 6/2018 |

(Continued)

OTHER PUBLICATIONS

Bibb et al., Cloning and analysis of the promoter region of the erythromycin resistance gene (ermF) of *Streptomyces erythraeus*. Gene, 1985, vol. 38: 215-226. (Year: 1985).*
LeClerc et al., Specificity of UV mutagenesis in the lac promoter of MI3lac hybrid phage DNA. Nature, 1982, vol. 297: 596-598. (Year: 1982).*
Satola et al., J. Bacteriol., 1992, vol. 174(5): 1448-1453. (Year: 1992).*
Short et al., Lambda ZAP: a bacteriophage lambda expression vector with in vivo excision properties. Nuc. Acids Res., 1988, vol. 16(1): 7583-7600. (Year: 1988).*
Browning et al., Local and global regulation of transcription initiation in bacteria. Nature, 2016, vol. 14: 638-650. (Year: 2016).*
Phillips et al., Diversity in lac Operon Regulation among Diverse *Escherichia coli* Isolates Depends on the Broader Genetic Background but is Not Explained by Genetic Relatedness. mBio, 2019, vol. 10(6), e02232-19, pp. 1-14. (Year: 2019).*

(Continued)

*Primary Examiner* — Ganapathirama Raghu
(74) *Attorney, Agent, or Firm* — HAMILTON, BROOK, SMITH & REYNOLDS, P.C.

(57) ABSTRACT

An improved promoter and a use thereof. An improvement is to mutate a nucleic acid sequence between −35 region and −10 region in a promoter region into recognition sites for an endonuclease. The improvement is used for overcoming the problem that a transcription or translation product of foreign genes under a strong promoter might be toxic to a host and cannot be cloned and avoiding the phenomena of false positives and false negatives during blue-white screening.

20 Claims, 1 Drawing Sheet

Specification includes a Sequence Listing.

(56)                     References Cited

FOREIGN PATENT DOCUMENTS

| CN | 108205614 A | 6/2018 |
|---|---|---|
| CN | 108221058 A | 6/2018 |
| CN | 108588102 A | 9/2018 |
| EP | 1 400 593 A1 | 3/2004 |
| EP | 1564294 A1 | 8/2005 |
| EP | 3 733 849 A1 | 11/2020 |
| EP | 3 733 851 A1 | 11/2020 |
| EP | 3 733 936 A1 | 11/2020 |
| EP | 3 734 602 A1 | 11/2020 |
| WO | 00/22112 A1 | 4/2000 |
| WO | 2011/091324 A2 | 7/2011 |
| WO | 2015/065964 A1 | 5/2015 |
| WO | 2015/115619 A1 | 8/2016 |
| WO | 2016/196805 A1 | 12/2016 |
| WO | 2017/075529 A1 | 5/2017 |
| WO | 2017/181735 A2 | 10/2017 |
| WO | 2019/128743 A1 | 7/2019 |
| WO | 2019/128744 A1 | 7/2019 |
| WO | 2019/128836 A1 | 7/2019 |
| WO | 2019/128837 A1 | 7/2019 |

OTHER PUBLICATIONS

Vlkova et al., Transcriptional control of the lacZ promoter is under directional and diversifying selection . bioRxiv, Mar. 18, 2022, pp. 1-51. (Year: 2022).*

Liu et al., A mutant spacer sequence between-35 and -10 elements makes the Plac promoter hyperactive and cAMP receptor protein-independent. PNAS., 2004, vol. 101(18): 6911-6916 (Year: 2004).*

Mandecki et al., Mutants of the lac promoter with large insertions and deletions between the CAP binding site and the-35 region. Gene, 1984, vol. 31: 263-267 (Year: 1984).*

Mandecki et al., lac Up-Promoter mutants with increased homology to the consensus promoter sequence. J. Bacteriol., 1985, vol. 164(3): 1353-1355. (Year: 1985).*

Alel-v2_NEB catalogue, one page down-loaded Apr. 12, 2024 (Year: 2024).*

BamHI_NEB catalogue, one page down-loaded Apr. 12, 2024. (Year: 2024).*

EcoRV_NEB catalogue, one page down-loaded Apr. 12, 2024. (Year: 2024).*

Pmll_NEB catalogue, one page down-loaded Apr. 12, 2024. (Year: 2024).*

Xhol_NEB catalogue, one page down-loaded Apr. 12, 2024. (Year: 2024).*

Stefano et al., Spacer mutations in the lac pS promoter. PNAS., 1982, vol. 79: 1069-1072. (Year: 1982).*

PCT International Preliminary Report on Patentability and Written Opinion for International Application No. PCT/CN2018/122309, entitled "Improved Promoter and Use Thereof" Mailed on Jul. 9, 2020.

PCT International Search Report and Written Opinion for International Application No. PCT/CN2018/122309, entitled "Improved Promoter and Use Thereof" Mailed on Mar. 22, 2019.

Hu, et al. "Associations between Hepatitis B Virus Basal Core Promoter/Pre-Core Region Mutations and the Risk of Acute-on-Chronic Liver Failure: a Meta-Analysis," Virology Journal, vol. 12, No. 87, Dec. 31, 2015, pp. 1-13.

Hsu, et al,. "Development and Applications of CRISPR-Cas9 for Genome Engineering," Cell. Jun. 5, 2014, 157(6), pp. 1262-1278.

Shen, "Modification and Expression of LipA Promoter in Bacillus Subtilis," Chinese Master's Theses Full-text Database Basic Science. Sep. 15, 2009, No. 9.

Yang, et al., "Application of the CRISPR/Cas9 Gene Editing Technology in Pigs," May 31, 2017, vol. 293, pp. 71-76. Heilongjiang Animal Science and Veterinary Medicine.

Rodriguez et al: "Characterizing wild-type and mutant promoters of the tetracycline resistance gene in pBR3 13", Nucleic Acids Research, vol. 6, No. 10, 1979, p. 3267-3287.

De Boer et al: "Construction of Three Hybrid Promoters and Their Properties in Escherichia coli", Proc. Miami. Winter. Symposia, vol. 19, Jan. 1982 (Jan. 1, 1982), pp. 309-327.

Moreno et al: "ihfA Gene of the Bacterium Myxococcus xanthus and Its Role in Activation of Carotenoid Genes by Blue Light", Journal of Bacteriology, American Society for Microbiology, vol. 183, No. 2, Jan. 2001, pp. 557-569.

Berg et al: "Specificity of Transposon Tn5 Insertion", Genetics Society of America, Dec. 1983, pp. 813-828.

Wang, et al: "Refinement of the Smallest Commonly Deleted Segment of Chromosome 20 in Malignant Myeloid Diseases and Development of a PAC-Based Physical and Transcription Map" Genomics, Academic Press, San Diego, US, vol. 67, No. 1, Jul. 1, 2000 (Jul. 1, 2000), pp. 28-39.

Database Geneseq (Online), "Escherichia coli lac promoter, SEQ ID 49." Retrieved from EBI accession No. GSN: BCD14467, Database accession No. BCD14467, Sep. 24, 2015 (Sep. 24, 2015).

Kostylev Maxim et al. "Cloning Should be Simple: Escherichia coli DH5[alpha]-Mediated Assembly of Multiple DNA Fragments with Short End Homologies", PLOS ONE, vol. 10, No. 9, Sep. 8, 2015 (Sep. 8, 2015).

Jain et al. "New improved lacZ gene fusion vectors", Gene, Elsevier Amsterdam, NL, vol. 133, No. 1, Oct. 29, 1993 (Oct. 29, 1993), pp. 99-102.

Extended European Search Report for EP Application No. 18893487, mailed on Dec. 15, 2021.

PCT International Search Report and Written Opinion for International Application No. PCT /CN2018/121326, entitled "Pig Whole Genome SGRNA Library, and Construction Method Therefor and Application Thereof" Mailed on Mar. 19, 2019.

PCT International Preliminary Report on Patentability and Written Opinion for International Application No. PCT/CN2018/121326, entitled "Pig Whole Genome SGRNA Library, and Construction Method Therefor and Application Thereof" Mailed on Jul. 9, 2020.

PCT International Preliminary Report on Patentability and Written Opinion for International Application No. PCT /CN2018/121328, entitled "Whole Genome SGRNA Library Constructing System and Application Thereof" Mailed on Jul. 9, 2020.

PCT International Search Report and Written Opinion for International Application No. PCT/CN2018/121328, entitled "Whole Genome SGRNA Library Constructing System and Application Thereof" Mailed on Mar. 19, 2019.

PCT International Preliminary Report on Patentability and Written Opinion for International Application No. PCT/CN2018/122312, entitled "Improved Promoter and Carrier Composed of Same and Application Thereof" Mailed on Jul. 9, 2020.

PCT International Search Report and Written Opinion for International Application No. PCT/CN2018/122312, entitled "Improved Promoter and Carrier Composed of Same and Application Thereof" Mailed on Jul. 9, 2020.

Miyazaki K., "Lethal ccdB gene-based zero-background vector for construction of shotgun libraries;" J Biosci Bioeng. Sep. 2010;110(3):372-3. doi: 10.1016/j.jbiosc.2010.02.016. Epub Apr. 1, 2010. PMID: 20547347.

Non-Final Office Action received for U.S. Appl. No. 16/916,032, mailed on Sep. 12, 2023, 21 pages.

Requirement for Restriction/Election received for U.S. Appl. No. 16/916,032, Mailed on Apr. 25, 2023, 12 pages.

Schildkraut et al., "The cleavage site for the restriction endonuclease EcoRV is 5'-GAT/ATC-3'", Gene, vol. 27, No. 3, Mar. 1984, pp. 327-329.

U.S. Final Office Action for U.S. Appl. No. 16/916,035, entitled "Promoter and carrier composed of same and application thereof," mailed on Aug. 23, 2022.

U.S. Non-Final Office Action for U.S. Appl. No. 16/916,035, entitled "Promoter and carrier composed of same and application thereof," mailed on Apr. 14, 2022.

U.S. Non-Final Office Action for U.S. Appl. No. 16/916,035, entitled "Promoter and carrier composed of same and application thereof," mailed on Apr. 20, 2023.

Zhou, Ming-Yi, and Celso E. Gomez-Sanchez. "Universal TA cloning." Current issues in molecular biology 2.1 (2000): 1-7 (Year: 2000).

(56)                    References Cited

OTHER PUBLICATIONS

Binder, Andreas, et al. "A modular plasmid assembly kit for multigene expression, gene silencing and silencing rescue in plants." PLoS One 9.2 (2014): e88218 (Year: 2014).

Dubendorf (Journal of molecular biology 219.1 (1991): 45-59) (Year: 1991).

Final Office Action for U.S. Appl. No. 16/916,032, mailed Mar. 29, 2024.

LeClerc, J. Eugene, and Nancy L. Istock. "M13 single stranded phage DNA with *E.coli* insert, including the regulatory region of the lac operon promoter . . . " Nature 297.5867 (1982): 596-598 (Year: 1982).

Non-Final Office Action received for U.S. Appl. No. 16/916,032, mailed on Nov. 8, 2024, 16 pages.

Notice of Allowance received for U.S. Appl. No. 16/916,032, mailed on Jul. 30, 2025, 13 pages.

* cited by examiner

SEQUENCE LISTING

```
<160> NUMBER OF SEQ ID NOS: 62

<210> SEQ ID NO 1
<211> LENGTH: 30
<212> TYPE: DNA
<213> ORGANISM: Artificial Sequence
<220> FEATURE:
<223> OTHER INFORMATION: Nucleic acid sequence between -35 region and
      -10 region in the promoter region of
      beta-galactosidase

<400> SEQUENCE: 1 tttcacacttt atgcttccgg ctcgtatgtt                                    30

<210> SEQ ID NO 2
<211> LENGTH: 18
<212> TYPE: DNA
<213> ORGANISM: Artificial Sequence
<220> FEATURE:
```

```
<223> OTHER INFORMATION: Nucleic acid sequence between -35 region and
      -10 region in the promoter region of
      beta-galactosidase

<400> SEQUENCE: 2
ctttatgctt ccggctcg                                             18

<210> SEQ ID NO 3
<211> LENGTH: 18
<212> TYPE: DNA
<213> ORGANISM: Artificial Sequence
<220> FEATURE:
<223> OTHER INFORMATION: Nucleic acid sequence between -35 region and
      -10 region of improved promoter

<400> SEQUENCE: 3
gatatcgctt ccggctcg                                             18

<210> SEQ ID NO 4
<211> LENGTH: 18
<212> TYPE: DNA
<213> ORGANISM: Artificial Sequence
<220> FEATURE:
<223> OTHER INFORMATION: Nucleic acid sequence between -35 region and
      -10 region of improved promoter

<400> SEQUENCE: 4
cttgatatct ccggctcg                                             18

<210> SEQ ID NO 5
<211> LENGTH: 18
<212> TYPE: DNA
<213> ORGANISM: Artificial Sequence
<220> FEATURE:
<223> OTHER INFORMATION: Nucleic acid sequence between -35 region and
      -10 region of improved promoter

<400> SEQUENCE: 5
ctttatgata tcggctcg                                             18

<210> SEQ ID NO 6
<211> LENGTH: 18
<212> TYPE: DNA
<213> ORGANISM: Artificial Sequence
<220> FEATURE:
<223> OTHER INFORMATION: Nucleic acid sequence between -35 region and
      -10 region of improved promoter

<400> SEQUENCE: 6
ctttatgctg atatctcg                                             18

<210> SEQ ID NO 7
<211> LENGTH: 18
<212> TYPE: DNA
<213> ORGANISM: Artificial Sequence
<220> FEATURE:
<223> OTHER INFORMATION: Nucleic acid sequence between -35 region and
      -10 region of improved promoter

<400> SEQUENCE: 7
ctttatgctt ccgatatc                                             18

<210> SEQ ID NO 8
<211> LENGTH: 18
<212> TYPE: DNA
<213> ORGANISM: Artificial Sequence
<220> FEATURE:
```

-continued

<223> OTHER INFORMATION: Nucleic acid sequence between -35 region and
       -10 region of improved promoter

<400> SEQUENCE: 8
ctttcacctt cgtgctcg                                                18

<210> SEQ ID NO 9
<211> LENGTH: 18
<212> TYPE: DNA
<213> ORGANISM: Artificial Sequence
<220> FEATURE:
<223> OTHER INFORMATION: Nucleic acid sequence between -35 region and
       -10 region of improved promoter

<400> SEQUENCE: 9
ctcgaggata tcggatcc                                                18

<210> SEQ ID NO 10
<211> LENGTH: 18
<212> TYPE: DNA
<213> ORGANISM: Artificial Sequence
<220> FEATURE:
<223> OTHER INFORMATION: Nucleic acid sequence between -35 region and
       -10 region of improved promoter

<400> SEQUENCE: 10
cacgtggctt ccggctcg                                                18

<210> SEQ ID NO 11
<211> LENGTH: 18
<212> TYPE: DNA
<213> ORGANISM: Artificial Sequence
<220> FEATURE:
<223> OTHER INFORMATION: Nucleic acid sequence between -35 region and
       -10 region of improved promoter

<400> SEQUENCE: 11
cttcacgtgt ccggctcg                                                18

<210> SEQ ID NO 12
<211> LENGTH: 18
<212> TYPE: DNA
<213> ORGANISM: Artificial Sequence
<220> FEATURE:
<223> OTHER INFORMATION: Nucleic acid sequence between -35 region and
       -10 region of improved promoter

<400> SEQUENCE: 12
ctttatcacg tgggctcg                                                18

<210> SEQ ID NO 13
<211> LENGTH: 18
<212> TYPE: DNA
<213> ORGANISM: Artificial Sequence
<220> FEATURE:
<223> OTHER INFORMATION: Nucleic acid sequence between -35 region and
       -10 region of improved promoter

<400> SEQUENCE: 13
ctttatgctc acgtgtcg                                                18

<210> SEQ ID NO 14
<211> LENGTH: 18
<212> TYPE: DNA
<213> ORGANISM: Artificial Sequence
<220> FEATURE:
<223> OTHER INFORMATION: Nucleic acid sequence between -35 region and

```
         -10 region of improved promoter

<400> SEQUENCE: 14
ctttatgctt cccacgtg                                                    18

<210> SEQ ID NO 15
<211> LENGTH: 41
<212> TYPE: DNA
<213> ORGANISM: Artificial Sequence
<220> FEATURE:
<223> OTHER INFORMATION: Primer

<400> SEQUENCE: 15
ccggaagcga tatctgtaaa gcctggggtg cctaatgagt g                          41

<210> SEQ ID NO 16
<211> LENGTH: 48
<212> TYPE: DNA
<213> ORGANISM: Artificial Sequence
<220> FEATURE:
<223> OTHER INFORMATION: Primer

<400> SEQUENCE: 16
ccccaggctt tacagatatc gcttccggct cgtatgttgt gtggaatt                   48

<210> SEQ ID NO 17
<211> LENGTH: 42
<212> TYPE: DNA
<213> ORGANISM: Artificial Sequence
<220> FEATURE:
<223> OTHER INFORMATION: Primer

<400> SEQUENCE: 17
gagccggaga tatcaagtgt aaagcctggg gtgcctaatg ag                         42

<210> SEQ ID NO 18
<211> LENGTH: 48
<212> TYPE: DNA
<213> ORGANISM: Artificial Sequence
<220> FEATURE:
<223> OTHER INFORMATION: Primer

<400> SEQUENCE: 18
caggctttac acttgatatc tccggctcgt atgttgtgtg gaattgtg                   48

<210> SEQ ID NO 19
<211> LENGTH: 42
<212> TYPE: DNA
<213> ORGANISM: Artificial Sequence
<220> FEATURE:
<223> OTHER INFORMATION: Primer

<400> SEQUENCE: 19
tacgagccga tatcataaag tgtaaagcct ggggtgccta at                         42

<210> SEQ ID NO 20
<211> LENGTH: 48
<212> TYPE: DNA
<213> ORGANISM: Artificial Sequence
<220> FEATURE:
<223> OTHER INFORMATION: Primer

<400> SEQUENCE: 20
gctttacact ttatgatatc ggctcgtatg ttgtgtggaa ttgtgagc                   48
```

```
<210> SEQ ID NO 21
<211> LENGTH: 42
<212> TYPE: DNA
<213> ORGANISM: Artificial Sequence
<220> FEATURE:
<223> OTHER INFORMATION: Primer

<400> SEQUENCE: 21
acatacgaga tatcagcata aagtgtaaag cctggggtgc ct                    42

<210> SEQ ID NO 22
<211> LENGTH: 48
<212> TYPE: DNA
<213> ORGANISM: Artificial Sequence
<220> FEATURE:
<223> OTHER INFORMATION: Primer

<400> SEQUENCE: 22
ttacacttta tgctgatatc tcgtatgttg tgtggaattg tgagcgga              48

<210> SEQ ID NO 23
<211> LENGTH: 42
<212> TYPE: DNA
<213> ORGANISM: Artificial Sequence
<220> FEATURE:
<223> OTHER INFORMATION: Primer

<400> SEQUENCE: 23
acaacataga tatcggaagc ataaagtgta aagcctgggg tg                    42

<210> SEQ ID NO 24
<211> LENGTH: 48
<212> TYPE: DNA
<213> ORGANISM: Artificial Sequence
<220> FEATURE:
<223> OTHER INFORMATION: Primer

<400> SEQUENCE: 24
cactttatgc ttccgatatc tatgttgtgt ggaattgtga gcggataa             48

<210> SEQ ID NO 25
<211> LENGTH: 48
<212> TYPE: DNA
<213> ORGANISM: Artificial Sequence
<220> FEATURE:
<223> OTHER INFORMATION: Primer

<400> SEQUENCE: 25
aacatacgag cacgaaggtg aaagtgtaaa gcctggggtg cctaatga             48

<210> SEQ ID NO 26
<211> LENGTH: 46
<212> TYPE: DNA
<213> ORGANISM: Artificial Sequence
<220> FEATURE:
<223> OTHER INFORMATION: Primer

<400> SEQUENCE: 26
tacactttca ccttcgtgct cgtatgttgt gtggaattgt gagcgg               46

<210> SEQ ID NO 27
<211> LENGTH: 50
<212> TYPE: DNA
<213> ORGANISM: Artificial Sequence
<220> FEATURE:
<223> OTHER INFORMATION: Primer
```

-continued

<400> SEQUENCE: 27
cataggatcc gatatcctcg agtgtaaagc ctggggtgcc taatgagtga           50

<210> SEQ ID NO 28
<211> LENGTH: 50
<212> TYPE: DNA
<213> ORGANISM: Artificial Sequence
<220> FEATURE:
<223> OTHER INFORMATION: Primer

<400> SEQUENCE: 28
tacactcgag gatatcggat cctatgttgt gtggaattgt gagcggataa           50

<210> SEQ ID NO 29
<211> LENGTH: 41
<212> TYPE: DNA
<213> ORGANISM: Artificial Sequence
<220> FEATURE:
<223> OTHER INFORMATION: Primer

<400> SEQUENCE: 29
ccggaagcca cgtgtgtaaa gcctggggtg cctaatgagt g           41

<210> SEQ ID NO 30
<211> LENGTH: 48
<212> TYPE: DNA
<213> ORGANISM: Artificial Sequence
<220> FEATURE:
<223> OTHER INFORMATION: Primer

<400> SEQUENCE: 30
ccccaggctt tacacacgtg gcttccggct cgtatgttgt gtggaatt           48

<210> SEQ ID NO 31
<211> LENGTH: 42
<212> TYPE: DNA
<213> ORGANISM: Artificial Sequence
<220> FEATURE:
<223> OTHER INFORMATION: Primer

<400> SEQUENCE: 31
gagccggaca cgtgaagtgt aaagcctggg gtgcctaatg ag           42

<210> SEQ ID NO 32
<211> LENGTH: 48
<212> TYPE: DNA
<213> ORGANISM: Artificial Sequence
<220> FEATURE:
<223> OTHER INFORMATION: Primer

<400> SEQUENCE: 32
caggctttac acttcacgtg tccggctcgt atgttgtgtg gaattgtg           48

<210> SEQ ID NO 33
<211> LENGTH: 42
<212> TYPE: DNA
<213> ORGANISM: Artificial Sequence
<220> FEATURE:
<223> OTHER INFORMATION: Primer

<400> SEQUENCE: 33
tacgagccca cgtgataaag tgtaaagcct ggggtgccta at           42

<210> SEQ ID NO 34
<211> LENGTH: 48

```
<212> TYPE: DNA
<213> ORGANISM: Artificial Sequence
<220> FEATURE:
<223> OTHER INFORMATION: Primer

<400> SEQUENCE: 34
gctttacact ttatcacgtg ggctcgtatg ttgtgtggaa ttgtgagc                48

<210> SEQ ID NO 35
<211> LENGTH: 42
<212> TYPE: DNA
<213> ORGANISM: Artificial Sequence
<220> FEATURE:
<223> OTHER INFORMATION: Primer

<400> SEQUENCE: 35
acatacgaca cgtgagcata aagtgtaaag cctggggtgc ct                      42

<210> SEQ ID NO 36
<211> LENGTH: 48
<212> TYPE: DNA
<213> ORGANISM: Artificial Sequence
<220> FEATURE:
<223> OTHER INFORMATION: Primer

<400> SEQUENCE: 36
ttacacttta tgctcacgtg tcgtatgttg tgtggaattg tgagcgga               48

<210> SEQ ID NO 37
<211> LENGTH: 42
<212> TYPE: DNA
<213> ORGANISM: Artificial Sequence
<220> FEATURE:
<223> OTHER INFORMATION: Primer

<400> SEQUENCE: 37
acaacataca cgtgggaagc ataaagtgta aagcctgggg tg                      42

<210> SEQ ID NO 38
<211> LENGTH: 48
<212> TYPE: DNA
<213> ORGANISM: Artificial Sequence
<220> FEATURE:
<223> OTHER INFORMATION: Primer

<400> SEQUENCE: 38
cactttatgc ttcccacgtg tatgttgtgt ggaattgtga gcggataa               48

<210> SEQ ID NO 39
<211> LENGTH: 348
<212> TYPE: DNA
<213> ORGANISM: Artificial Sequence
<220> FEATURE:
<223> OTHER INFORMATION: lacZ gene

<400> SEQUENCE: 39
atgaccatgc tcgagccaag cttgcatgca ggcctctgca gtcgacgggc ccgggatccg   60
atatctagat gcattcgcga ggtaccgagc tcgaattcac tggccgtcgt tttacaacgt   120
cgtgactggg aaaaccctgg cgttacccaa cttaatcgcc ttgcagcaca tccccctttc   180
gccagctggc gtaatagcga agaggcccgc accgatcgcc cttcccaaca gttgcgcagc   240
ctgaatggcg aatggcgcct gatgcggtat tttctcctta cgcatctgtg cggtatttca   300
caccgcatat ggtgcactct cagtacaatc tgctctgatg ccgcatag              348
```

-continued

```
<210> SEQ ID NO 40
<211> LENGTH: 348
<212> TYPE: DNA
<213> ORGANISM: Artificial Sequence
<220> FEATURE:
<223> OTHER INFORMATION: Codon-optimized lacZ gene

<400> SEQUENCE: 40
atgaccatgc tggaaccgag cctgcatgca ggtctgtgca gccgtcgtgc acgcgatccg      60
attagccgct gcattcgcga agtgccgagc agcaatagcc tggccgtggt gctgcagcgt     120
cgcgattggg aaaatccggg tgtgacccag ctgaatcgcc tggcagcaca tccgccgttt     180
gccagctggc gtaatagcga agaagcacgc accgatcgtc cgagccagca gctgcgtagc     240
ctgaatggcg aatggcgcct gatgcgctat tttctgctga cccatctgtg cggcattagc     300
catcgcattt ggtgcaccct gagcaccatt tgcagcgatg ccgcctaa                  348

<210> SEQ ID NO 41
<211> LENGTH: 55
<212> TYPE: DNA
<213> ORGANISM: Artificial Sequence
<220> FEATURE:
<223> OTHER INFORMATION: Primer

<400> SEQUENCE: 41
atgcaggctc ggttccagca tggtcatagc tgtttcctgt gtgaaattgt tatcc           55

<210> SEQ ID NO 42
<211> LENGTH: 55
<212> TYPE: DNA
<213> ORGANISM: Artificial Sequence
<220> FEATURE:
<223> OTHER INFORMATION: Primer

<400> SEQUENCE: 42
agcaccattt gcagcgatgc cgcctaatta agccagcccc gacacccgcc aacac           55

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
ttcatacagc aggctatgtt tagg                                             24

<210> SEQ ID NO 44
<211> LENGTH: 24
<212> TYPE: DNA
<213> ORGANISM: Artificial Sequence
<220> FEATURE:
<223> OTHER INFORMATION: Primer

<400> SEQUENCE: 44
cctaaacata gcctgctgta tgaa                                             24

<210> SEQ ID NO 45
<211> LENGTH: 48
<212> TYPE: DNA
<213> ORGANISM: Artificial Sequence
<220> FEATURE:
<223> OTHER INFORMATION: Primer

<400> SEQUENCE: 45
```

-continued

```
taagccgata ctgtattttt tatccatagc tgtttcctgt gtgaaatt                    48

<210> SEQ ID NO 46
<211> LENGTH: 48
<212> TYPE: DNA
<213> ORGANISM: Artificial Sequence
<220> FEATURE:
<223> OTHER INFORMATION: Primer

<400> SEQUENCE: 46
aatttcacac aggaaacagc tatggataaa aaatacagta tcggctta                    48

<210> SEQ ID NO 47
<211> LENGTH: 47
<212> TYPE: DNA
<213> ORGANISM: Artificial Sequence
<220> FEATURE:
<223> OTHER INFORMATION: Primer

<400> SEQUENCE: 47
aatggtcagg atccgttgaa tgggcggatg ctaattacta tctcccg                     47

<210> SEQ ID NO 48
<211> LENGTH: 47
<212> TYPE: DNA
<213> ORGANISM: Artificial Sequence
<220> FEATURE:
<223> OTHER INFORMATION: Primer

<400> SEQUENCE: 48
tgaagaacct cgagttatgc tctataaagt aggcataaac acccagc                     47

<210> SEQ ID NO 49
<211> LENGTH: 42
<212> TYPE: DNA
<213> ORGANISM: Artificial Sequence
<220> FEATURE:
<223> OTHER INFORMATION: Primer

<400> SEQUENCE: 49
atacgagccg gagaatcaag tgtaaagcct ggggtgccta at                          42

<210> SEQ ID NO 50
<211> LENGTH: 42
<212> TYPE: DNA
<213> ORGANISM: Artificial Sequence
<220> FEATURE:
<223> OTHER INFORMATION: Primer

<400> SEQUENCE: 50
gctttacact tgattctccg gctcgtatgt tgtgtggaat tg                          42

<210> SEQ ID NO 51
<211> LENGTH: 42
<212> TYPE: DNA
<213> ORGANISM: Artificial Sequence
<220> FEATURE:
<223> OTHER INFORMATION: Primer

<400> SEQUENCE: 51
tacgagccgg agattcaagt gtaaagcctg gggtgcctaa tg                          42

<210> SEQ ID NO 52
<211> LENGTH: 43
<212> TYPE: DNA
```

<213> ORGANISM: Artificial Sequence
<220> FEATURE:
<223> OTHER INFORMATION: Primer

<400> SEQUENCE: 52
ggctttacac ttgaatctcc ggctcgtatg ttgtgtggaa ttg                          43

<210> SEQ ID NO 53
<211> LENGTH: 42
<212> TYPE: DNA
<213> ORGANISM: Artificial Sequence
<220> FEATURE:
<223> OTHER INFORMATION: Primer

<400> SEQUENCE: 53
atacgagccg gagatcaagt gtaaagcctg gggtgcctaa tg                           42

<210> SEQ ID NO 54
<211> LENGTH: 42
<212> TYPE: DNA
<213> ORGANISM: Artificial Sequence
<220> FEATURE:
<223> OTHER INFORMATION: Primer

<400> SEQUENCE: 54
ggctttacac ttgatctccg gctcgtatgt tgtgtggaat tg                           42

<210> SEQ ID NO 55
<211> LENGTH: 55
<212> TYPE: DNA
<213> ORGANISM: Artificial Sequence
<220> FEATURE:
<223> OTHER INFORMATION: Primer

<400> SEQUENCE: 55
atgcaggctc ggttccagca tggtcatagc tgtttcctgt gtgaaattgt tatcc            55

<210> SEQ ID NO 56
<211> LENGTH: 55
<212> TYPE: DNA
<213> ORGANISM: Artificial Sequence
<220> FEATURE:
<223> OTHER INFORMATION: Primer

<400> SEQUENCE: 56
agcaccattt gcagcgatgc cgcctaatta agccagcccc gagtagctag acagg            55

<210> SEQ ID NO 57
<211> LENGTH: 55
<212> TYPE: DNA
<213> ORGANISM: Artificial Sequence
<220> FEATURE:
<223> OTHER INFORMATION: Primer

<400> SEQUENCE: 57
atgcaggctc ggttccagca tggtcatagc tgtttcctgt gtgaaattgt tatcc            55

<210> SEQ ID NO 58
<211> LENGTH: 55
<212> TYPE: DNA
<213> ORGANISM: Artificial Sequence
<220> FEATURE:
<223> OTHER INFORMATION: Primer

<400> SEQUENCE: 58
agcaccattt gcagcgatgc cgcctaatta agccagcccc gacaccgcc aacac             55

-continued

```
<210> SEQ ID NO 59
<211> LENGTH: 18
<212> TYPE: DNA
<213> ORGANISM: Artificial Sequence
<220> FEATURE:
<223> OTHER INFORMATION: Nucleic acid sequence between -35 region and
      -10 region of improved promoter

<400> SEQUENCE: 59
cttgatatct ccggctcg                                                        18

<210> SEQ ID NO 60
<211> LENGTH: 17
<212> TYPE: DNA
<213> ORGANISM: Artificial Sequence
<220> FEATURE:
<223> OTHER INFORMATION: Mutant plasmid pUC57-lacZ-Mu-2A

<400> SEQUENCE: 60
cttgattctc cggctcg                                                         17

<210> SEQ ID NO 61
<211> LENGTH: 17
<212> TYPE: DNA
<213> ORGANISM: Artificial Sequence
<220> FEATURE:
<223> OTHER INFORMATION: Mutant plasmid pUC57-lacZ-Mu-2B

<400> SEQUENCE: 61
cttgaatctc cggctcg                                                         17

<210> SEQ ID NO 62
<211> LENGTH: 16
<212> TYPE: DNA
<213> ORGANISM: Artificial Sequence
<220> FEATURE:
<223> OTHER INFORMATION: Mutant plasmid pUC57-lacZ-Mu-2C

<400> SEQUENCE: 62
cttgatctcc ggctcg                                                          16
```

PROMOTER AND USE THEREOF

RELATED APPLICATIONS

This application is a continuation-in-part of International Application No. PCT/CN2018/122309, which designated the United States and was filed on Dec. 20, 2018, published in Chinese, which claims priority under 35 U.S.C. § 119 or 365 to CN application No. 201711490227.9, filed Dec. 29, 2017. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:

a) File name: 58241000002_SEQUENCELISTING.txt; created Oct. 13, 2020, 13 KB in size.

TECHNICAL FIELD

The present application belongs to the field of genetic engineering, and relates to an improved promoter and a use thereof, in particular, to an improved promoter, a cloning vector with the improved promoter, a host cell with the cloning vector and uses thereof.

BACKGROUND

A polymerase chain reaction (PCR) technology is a major breakthrough in the fields of molecular biology and genetic engineering. After the PCR technology was developed, a technology for cloning PCR products into vectors (generally plasmids) has also been developed. Commonly-used and relatively simple cloning methods include TA cloning and blunt-end ligations. The PCR product amplified by *Thermus aquaticus* (Taq) enzymes contains a dAMP tail which can be ligated to a vector containing a T-terminus (T vector) under the action of T4 ligases, and this is the TA cloning. High-fidelity DNA polymerases generally contain 3'-5' exonuclease activity, and the PCR products amplified by the high-fidelity DNA polymerases are blunt ends. These fragments are ligated to blunt-end vectors under the action of T4 ligases, which are the blunt-end ligations. These two methods have a common feature that the PCR products do not need to be treated in advance with special enzymes but are directly ligated to the vectors, which is simple and easily operated.

At present, commercially available T vectors and vectors that can be used for blunt-end cloning are generally based on the principle of blue-white screening. The blue-white screening is the most commonly used screening scheme to separate empty vectors from vectors with inserts. In this method, a reporter gene LacZα is used as a marker gene for the blue-white screening. However, vectors based on principle of blue-white screening have the following problems during cloning: (1) due to the use of a strong promoter, the transcription and translation of foreign genes can be initiated in large quantities, which causes transcription or translation products of some foreign genes with complex structures to be toxic to hosts and cannot be cloned; (2) due to residual exonuclease activity of restriction enzymes when vectors are digested, repeated freezing and thawing of the digested vectors, long-term storage of digested linearized vectors and other factors, the prepared vectors lack 1-2 bases at digestion sites, leading to frameshift mutation of a lacZα gene, so that a clone without a foreign gene becomes white due to the frameshift mutation of the LacZα gene, resulting in a large number of false positive clones; (3) when a small foreign DNA fragment is cloned and a reading frame of the lacZα gene is not changed by inserting the foreign DNA, a false negative phenomenon that a plate is rich in blue spots will be caused; (4) when a foreign DNA fragment larger than 2 kb is cloned with a blunt-end vector, a few white spots and many blue spots are present, and the few white spots might grow together with the blue spots, so that white single clones are few, and it is difficult to select a sufficient number of positive clones. In addition, the blue-white screening further requires expensive and toxic chemical substances such as X-gal and IPTG.

Any DNA sequence that can be independently bound to a transcription factor and initiate transcription may be referred to as a promoter. A region recognizable by a σ factor in the promoter has very conserved sequence characteristics. Two sequences (referred to as −10 region and −35 region) about 10 nt and 35 nt upstream of a transcription starting site (+1) have a decisive effect on the recognition of the σ factor, so these two sequences are referred to as narrow promoters or core promoters. Other than the core promoters, sequences upstream of −35 region might also have an effect on transcription strength. These sequences are referred to as UP elements.

SUMMARY

Therefore, the present application provides an improved promoter and a use thereof, so as to solve the problems that a prepared cloning vector fails in cloning, or a large number of false positive or negative clones are produced in the existing art.

To achieve the object, the present application adopts technical solutions described below.

In a first aspect, the present application provides an improved promoter. The improved promoter is obtained by mutating a nucleic acid sequence between −35 region and −10 region in a promoter region into recognition sites for an endonuclease.

In the present application, a change in the number of nucleic acids between −35 region and −10 region in a prokaryote will affect a level of gene transcription activity. The nucleic acid sequence between −35 region and −10 region in the promoter region is mutated to be recognized by the endonuclease. During cloning, a vector is prepared as a linearized vector, and then a foreign gene is ligated to the linearized vector, so that an expression-regulating gene of the promoter has decreased activity and a reduced expression amount, and then functions.

The recognition sites for the endonuclease refer to sites recognizable by any endonuclease, and the endonuclease is not limited and is selected mainly based on the convenience of experimental operations of those skilled in the art, as long as a successful mutation can be achieved by mutating one or several bases.

According to the present application, the improved promoter is obtained by mutating a nucleic acid sequence between −35 region and −10 region in a promoter region of a β-galactosidase into the recognition sites for the endonuclease.

In the present application, for a promoter of the β-galactosidase, the nucleic acid sequence between −35 region and −10 region in a strong promoter region is mutated into the recognition sites for the endonuclease that can be recognized, but it is cleaved into the linearized vector and inserted with a foreign fragment, so that a strong promoter of the β-galactosidase has significantly decreased activity due to the insertion of a foreign DNA fragment, an expression amount of a lacZα gene is significantly reduced, and a colony containing a recombinant plasmid is white, thereby overcoming the problem that a strong promoter in a vector based on blue-white screening initiates the transcription or translation of foreign genes and a transcription or translation product might be toxic to a host and cannot be cloned, avoiding the deficiency that frameshift mutation of the lacZα gene due to a lack of 1-2 bp of the vector at digestion sites results in false positive clones, and eliminating a false negative phenomenon that a plate is rich in blue spots due to a small fragment of foreign DNA and a reading frame of the lacZα gene which is unchanged by inserting the foreign DNA.

According to the present application, the nucleic acid sequence between −35 region and −10 region in the promoter region of the β-galactosidase is shown by SEQ ID NOs: 1-2, where nucleic acid sequences shown by SEQ ID NOs: 1-2 are as follows:

```
SEQ ID NO. 1:
5'-TTTACACTTTATGCTTCCGGCTCGTATGTT-3';
and

SEQ ID NO. 2:
5'-CTTTATGCTTCCGGCTCG-3'.
```

In the present application, an RNA polymerase II is generally bound at sites from −35 region to −10 region which are very important. An RNA polymerase can be in contact with a base in −35 and −10 sequences and a phosphate group in a primary DNA strand. A promoter farther from a common sequence has lower activity. The applicant has found that the foreign gene can be inserted by mutating a sequence from −35 region to −10 region, especially the sequence shown by SEQ ID NO: 2, so as to significantly reduce the expression amount of the lacZα gene.

According to the present application, the endonuclease may be selected by those skilled in the art as required, and different recognition sites for the endonuclease may be selected according to different sequences to be mutated in the promoter region. In the present application, the endonuclease is selected from, but is not limited to, any one or a combination of at least two of EcoRV, AleI, BamHI, XhoI and PmlI.

According to the present application, a nucleic acid sequence between −35 region and −10 region of the improved promoter is shown by SEQ ID NOs: 3-14, where nucleic acid sequences shown by SEQ ID NOs: 3-14 are as follows:

```
SEQ ID NO. 3:
5'-GATATCGCTTCCGGCTCG-3';

SEQ ID NO. 4:
5'- CTTGATATCTCCGGCTCG-3';

SEQ ID NO. 5:
5'-CTTTATGATATCGGCTCG-3';

SEQ ID NO. 6:
5'-CTTTATGCTGATATCTCG-3';

SEQ ID NO. 7:
5'-CTTTATGCTTCCGATATC-3';
```

4

```
-continued
SEQ ID NO. 8:
5'-CTTTCACCTTCGTGCTCG-3';

SEQ ID NO. 9:
5'-CTCGAGGATATCGGATCC-3';

SEQ ID NO. 10:
5'-CACGTGGCTTCCGGCTCG-3';

SEQ ID NO. 11:
5'-CTTCACGTGTCCGGCTCG-3';

SEQ ID NO. 12:
5'-CTTTATCACGTGGGCTCG-3';

SEQ ID NO. 13:
5'-CTTTATGCTCACGTGTCG-3';
and

SEQ ID NO. 14:
5'-CTTTATGCTTCCCACGTG-3'.
```

In a second aspect, the present application provides a vector including the improved promoter described in the first aspect.

According to the present application, the vector further includes a gene of interest, where the gene of interest is operably ligated between the recognition sites for the endonuclease of the improved promoter.

In the present application, those skilled in the art may select the vector according to requirements. The selection of the vector will not affect a function of the promoter. The vector may be a cloning vector and/or an expression vector. The cloning vector is used for cloning a protein of interest, and the expression vector is used for expressing the protein of interest. The promoter may function on either the cloning vector or the expression vector. The vector is preferably the cloning vector, and the cloning vector may be, for example, a high-copy cloning vector pUC57, a low-copy cloning vector pCK or a single-copy cloning vector, each of which may carry the promoter of the present application, so as to carry out subsequent experiments without affecting the vector itself. The vector carrying the promoter of the present application is still a high-copy cloning vector, a low-copy cloning vector or a single-copy cloning vector.

In a third aspect, the present application provides a host cell, including the vector described in the second aspect.

According to the present application, the host cell is *Escherichia coli*, and a C-terminal ω-fragment of a β-galactosidase of the *Escherichia coli* is only encoded.

In the present application, a lacZα gene of the cloning vector encodes an N-terminal α-fragment of the β-galactosidase (lacZ), and the C-terminal ω-fragment of the β-galactosidase of the *Escherichia coli* is only encoded. Although none of encoded fragments of a host and a plasmid have galactosidase activity, when they exist at the same time, the α-fragment and the ω-fragment may form the β-galactosidase with enzymatic activity through α-complementation, and the β-galactosidase may cleave a colorless compound, X-gal (5-bromo-4-chloro-3-indole-β-D-galactoside), into galactose and a dark blue substance, 5-bromo-4-indigo which may make the whole colony appear blue. After foreign DNA is inserted into the promoter region of the β-galactosidase of the cloning vector of the present application, an expression amount of lacZα is significantly reduced, and a large amount of β-galactosidases with enzymatic activity cannot be effectively formed through the α-complementation, and eventually the colony appears white.

In a fourth aspect, the present application provides a method for preparing the vector described in the second aspect. The method includes steps described below.

(1) A primer is designed according to recognition sites for an endonuclease to be mutated into, and an original promoter and an expression-regulating gene of the original promoter are used as a template for PCR amplification, to obtain a product with an improved promoter.

(2) The product in step (1) is cyclized by a Gibson recombination method to obtain a vector with the promoter.

(3) The vector in step (2) is linearized.

(4) A gene of interest is ligated to the linearized vector in step (3) to obtain the vector.

According to the present application, a nucleic acid sequence of the primer in step (1) is shown by SEQ ID NOs: 15-38.

In the present application, in a plasmid constructed by performing PCR amplification on pUC57-lacZ or pCK-lacZ with a primer pair of nucleic acid sequences shown by SEQ ID NOs: 15-16, a nucleic acid sequence shown by SEQ ID NO: 2 is mutated into a nucleic acid sequence shown by SEQ ID NO: 3.

In a plasmid constructed by performing PCR amplification on pUC57-lacZ or pCK-lacZ with a primer pair of nucleic acid sequences shown by SEQ ID NOs: 17-18, the nucleic acid sequence shown by SEQ ID NO: 2 is mutated into a nucleic acid sequence shown by SEQ ID NO: 4.

In a plasmid constructed by performing PCR amplification on pUC57-lacZ or pCK-lacZ with a primer pair of nucleic acid sequences shown by SEQ ID NOs: 19-20, the nucleic acid sequence shown by SEQ ID NO: 2 is mutated into a nucleic acid sequence shown by SEQ ID NO: 5.

In a plasmid constructed by performing PCR amplification on pUC57-lacZ or pCK-lacZ with a primer pair of nucleic acid sequences shown by SEQ ID NOs: 21-22, the nucleic acid sequence shown by SEQ ID NO: 2 is mutated into a nucleic acid sequence shown by SEQ ID NO: 6.

In a plasmid constructed by performing PCR amplification on pUC57-lacZ or pCK-lacZ with a primer pair of nucleic acid sequences shown by SEQ ID NOs: 23-24, the nucleic acid sequence shown by SEQ ID NO: 2 is mutated into a nucleic acid sequence shown by SEQ ID NO: 7.

In a plasmid constructed by performing PCR amplification on pUC57-lacZ or pCK-lacZ with a primer pair of nucleic acid sequences shown by SEQ ID NOs: 25-26, the nucleic acid sequence shown by SEQ ID NO: 2 is mutated into a nucleic acid sequence shown by SEQ ID NO: 8.

In a plasmid constructed by performing PCR amplification on pUC57-lacZ or pCK-lacZ with a primer pair of nucleic acid sequences shown by SEQ ID NOs: 27-28, the nucleic acid sequence shown by SEQ ID NO: 2 is mutated into a nucleic acid sequence shown by SEQ ID NO: 9.

In a plasmid constructed by performing PCR amplification on pCC1-lacZ with a primer pair of nucleic acid sequences shown by SEQ ID NOs: 29-30, the nucleic acid sequence shown by SEQ ID NO: 2 is mutated into a nucleic acid sequence shown by SEQ ID NO: 10.

In a plasmid constructed by performing PCR amplification on pCC1-lacZ with a primer pair of nucleic acid sequences shown by SEQ ID NOs: 31-32, the nucleic acid sequence shown by SEQ ID NO: 2 is mutated into a nucleic acid sequence shown by SEQ ID NO: 11.

In a plasmid constructed by performing PCR amplification on pCC1-lacZ with a primer pair of nucleic acid sequences shown by SEQ ID NOs: 33-34, the nucleic acid sequence shown by SEQ ID NO: 2 is mutated into a nucleic acid sequence shown by SEQ ID NO: 12.

In a plasmid constructed by performing PCR amplification on pCC1-lacZ with a primer pair of nucleic acid sequences shown by SEQ ID NOs: 35-36, the nucleic acid sequence shown by SEQ ID NO: 2 is mutated into a nucleic acid sequence shown by SEQ ID NO: 13.

In a plasmid constructed by performing PCR amplification on pCC1-lacZ with a primer pair of nucleic acid sequences shown by SEQ ID NOs: 37-38, the nucleic acid sequence shown by SEQ ID NO: 2 is mutated into a nucleic acid sequence shown by SEQ ID NO: 14.

According to the present application, the linearizing in step (3) is performed through endonuclease digestion and/or the PCR amplification.

According to the present application, before step (1), the method further includes performing codon optimization on the expression-regulating gene.

According to the present application, the expression-regulating gene is a lacZ gene whose nucleic acid sequence is shown by SEQ ID NO: 39, where the nucleic acid sequence shown by SEQ ID NO: 39 is as follows:

```
ATGACCATGCTCGAGCCAAGCTTGCATGCAGGCCTCTGCAGTCG

ACGGGCCCGGGATCCGATATCTAGATGCATTCGCGAGGTACCGA

GCTCGAATTCACTGGCCGTCGTTTTACAACGTCGTGACTGGGAA

AACCCTGGCGTTACCCAACTTAATCGCCTTGCAGCACATCCCCC

TTTCGCCAGCTGGCGTAATAGCGAAGAGGCCCGCACCGATCGCC

CTTCCCAACAGTTGCGCAGCCTGAATGGCGAATGGCGCCTGATG

CGGTATTTTCTCCTTACGCATCTGTGCGGTATTTCACACCGCAT

ATGGTGCACTCTCAGTACAATCTGCTCTGATGCCGCATAG.
```

According to the present application, the lacZ gene is subjected to the codon optimization, and a nucleic acid sequence of the lacZ gene subjected to the codon optimization is shown by SEQ ID NO: 40, where the nucleic acid sequence shown by SEQ ID NO: 40 is as follows:

```
ATGACCATGCTGGAACCGAGCCTGCATGCAGGTCTGTGCAGCCG

TCGTGCACGCGATCCGATTAGCCGCTGCATTCGCGAAGTGCCGA

GCAGCAATAGCCTGGCCGTGGTGCTGCAGCGTCGCGATTGGGAA

AATCCGGGTGTGACCCAGCTGAATCGCCTGGCAGCACATCCGCC

GTTTGCCAGCTGGCGTAATAGCGAAGAAGCACGCACCGATCGTC

CGAGCCAGCAGCTGCGTAGCCTGAATGGCGAATGGCGCCTGATG

CGCTATTTTCTGCTGACCCATCTGTGCGGCATTAGCCATCGCAT

TTGGTGCACCCTGAGCACCATTTGCAGCGATGCCGCCTAA.
```

In a fifth aspect, the present application provides a method for preparing a protein of interest. The method includes a step described below.

The host cell described in the third aspect is cultivated under conditions suitable for an expression of the protein of interest to obtain the protein of interest; where a vector in the host cell is an expression vector, and the protein of interest is a protein encoded by a gene of interest.

In a sixth aspect, the present application provides a kit, including the improved promoter described in the first aspect, the vector described in the second aspect or the host cell described in the third aspect.

Compared with the existing art, the present application has beneficial effects described below.

(1) In the present application, the nucleic acid sequence between −35 region and −10 region in the promoter region is mutated to be recognized by the endonuclease. During cloning, the vector is prepared as the linearized vector, and then the foreign gene is ligated to the linearized vector, so that the promoter has decreased activity, the expression amount of the expression-regulating gene is reduced, and then the promoter functions.

(2) The present application has a significant effect on the promoter of the β-galactosidase. The nucleic acid sequence between −35 region and −10 region in the strong promoter region is mutated into the recognition sites for the endonuclease that can be recognized. When it is cleaved into the linearized vector and inserted with the foreign fragment, the strong promoter of the β-galactosidase has significantly decreased activity due to the insertion of the foreign DNA fragment, the expression amount of the lacZα gene is significantly reduced, and the colony containing the recombinant plasmid appear white.

(3) The present application can overcome the problem that the strong promoter in the vector based on the blue-white screening initiates the transcription or translation of foreign genes and the transcription or translation product might be toxic to the host and cannot be cloned, avoid the deficiency that the frameshift mutation of the lacZα gene due to the lack of 1-2 bp of the vector at digestion sites results in the false positive clones, and eliminate the false negative phenomenon that the plate is rich in blue spots due to the small fragment of foreign DNA and the reading frame of the lacZα gene which is unchanged by inserting the foreign DNA.

(4) A method for constructing the cloning vector of the present application is simple and easy to operate, has high efficiency, and can construct the cloning vector in a short time.

DETAILED DESCRIPTION

Figure 1:
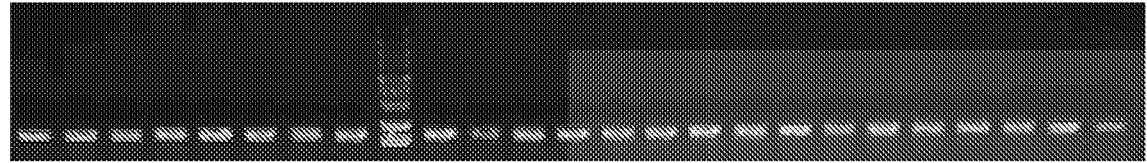
FIG. 1 is an electrophoresis diagram of colony PCR identification in Example 2 of the present application, where a size of a DNA marker is 0.1 kb, 0.25 kb, 0.5 kb, 0.75 kb, 1 kb, 1.5 kb, 2 kb, 3 kb and 5 kb.

To further elaborate on the technical means adopted and the effects achieved in the present application, the technical solutions of the present application are further described below through specific embodiments, but the present application is not limited to the scope of the embodiments.

The present application adopts conventional techniques and methods in the fields of genetic engineering and molecular biology, and general reference literature provides definitions and methods known to those skilled in the art. However, those skilled in the art may adopt other conventional methods, experimental schemes and reagents in the art on the basis of the technical solutions described in the present application without being limited by specific embodiments of the present application.

Experiments without specific techniques or conditions noted in the examples are conducted according to techniques or conditions described in the literature in the art or a product specification. The reagents or instruments used without manufacturers are conventional products commercially available through proper channels.

Explanation of Terms

LacZ gene: a gene widely used in gene expression regulation researches. An encoded β-galactosidase (β-gal) is a tetramer composed of 4 subunits and can catalyze a hydrolysis of lactose. The β-gal is relatively stable, appears blue when stained with X-Gal as a substrate, and is easy to detect and observe. Many advantages of the LacZ gene make it a commonly-used marker gene in genetic engineering experiments such as screening of transformed strains and β-galactosidase color test method, that is, blue-white screening.

LacZα gene: an N-terminal α-fragment for encoding the β-galactosidase (lacZ). The β-galactosidase with enzymatic activity may be formed through α-complementation and cleave a colorless compound, X-gal (5-bromo-4-chloro-3-indole-β-D-galactoside), into galactose and a dark blue substance, 5-bromo-4-indigo.

Endonuclease: an enzyme that can hydrolyze a phosphodiester bond inside a molecular chain to generate oligonucleotides among nucleic acid hydrolases.

PCR technology: a polymerase chain reaction, in which DNA is denatured in vitro at a high temperature of 95° C. to be single-stranded, a primer combines with a single strand at a low temperature (generally about 60° C.) based on a principle of complementary base pairing, the temperature is adjusted to an optimal reaction temperature of a DNA polymerase (about 72° C.) at which the DNA polymerase synthesizes a complementary strand along a direction from phosphate to five-carbon sugar (5'-3'). A PCR instrument based on polymerases is in fact a temperature control device and can control the temperature well between a denaturation temperature, a renaturation temperature and an extension temperature.

Materials:

Kanamycin-resistant pUC57 plasmid Genewiz Inc. Suzhou pCK plasmid Genewiz Inc. Suzhou Chloramphenicol-resistant pCC1TM plasmid EPICENTRE Top10F' competent cell Invitrogen Restriction enzymes: EcoRV, AleI, BamHI, XhoI NEB T4 DNA ligase NEB lambdaDNA NEB Gibson Assembly® Master Mix kit NEB Primer synthesis Genewiz Inc. Suzhou

Example 1: Codon Optimization of a lacZα Gene

The codon optimization of the lacZα gene includes a step described below.

The codon optimization was conducted on the lacZα gene (SEQ ID NO: 39) in a pUC57 plasmid using codon optimization software (developed by Genewiz Inc. Suzhou), where the optimized lacZα gene was synthesized by Genewiz Inc. Suzhou. A nucleotide sequence is shown by SEQ ID NO: 39, specifically:

the lacZα gene (SEQ ID NO. 39):
ATGACCATGCTCGAGCCAAGCTTGCATGCAGGCCTCTGCAGTCG

ACGGGCCCGGGATCCGATATCTAGATGCATTCGCGAGGTACCGA

GCTCGAATTCACTGGCCGTCGTTTTACAACGTCGTGACTGGGAA

AACCCTGGCGTTACCCAACTTAATCGCCTTGCAGCACATCCCCC

TTTCGCCAGCTGGCGTAATAGCGAAGAGGCCCGCACCGATCGCC

CTTCCCAACAGTTGCGCAGCCTGAATGGCGAATGGCGCCTGATG

CGGTATTTTCTCCTTACGCATCTGTGCGGTATTTCACACCGCAT

ATGGTGCACTCTCAGTACAATCTGCTCTGATGCCGCATAG;

the optimized lacZα gene (SEQ ID NO. 40):
ATGACCATGCTGGAACCGAGCCTGCATGCAGGTCTGTGCAGCCG

TCGTGCACGCGATCCGATTAGCCGCTGCATTCGCGAAGTGCCGA

GCAGCAATAGCCTGGCCGTGGTGCTGCAGCGTCGCGATTGGGAA

AATCCGGGTGTGACCCAGCTGAATCGCCTGGCAGCACATCCGCC

GTTTGCCAGCTGGCGTAATAGCGAAGAAGCACGCACCGATCGTC

CGAGCCAGCAGCTGCGTAGCCTGAATGGCGAATGGCGCCTGATG

CGCTATTTTCTGCTGACCCATCTGTGCGGCATTAGCCATCGCAT

TTGGTGCACCCTGAGCACCATTTGCAGCGATGCCGCCTAA.

Example 2 Construction of a High-Copy Cloning Vector

A method for constructing the high-copy cloning vector includes specific steps described below.

(I) The lacZα gene of pUC57 (kanamycin resistance) was replaced with the optimized lacZα gene in Example 1, specifically including steps described below.

(1) The kanamycin-resistant pUC57 plasmid was used as a template and SEQ ID NOs: 41-42 were used as primers for PCR amplification. Specific sequences are as follows:

SEQ ID NO. 41 (forward primer):
ATGCAGGCTCGGTTCCAGCATGGTCATAGCTGTTTCCTGTGTGA

AATTGTTATCC;

SEQ ID NO. 42 (reverse primer):
AGCACCATTTGCAGCGATGCCGCCTAATTAAGCCAGCCCCGACA

CCCGCCAACAC.

A PCR system is shown in Table 1.

TABLE 1

| Template | About 50 ng, 0.5 μL |
|---|---|
| Forward primer | 10 pM, 0.5 μL |
| Reverse primer | 10 pM, 0.5 μL |
| dNTP | 5 mM each, 0.5 μL |
| 5 × PCR buffer | 10 μL |
| pfu DNA polymerase | 5 U/μL 0.5 μL |
| H₂O | 37.5 μL |

One group uses water as a sample for negative control. Reaction conditions are listed in Table 2.

TABLE 2

| Amplification program | |
|---|---|
| Reaction Program | Number of Cycles |
| 95° C. 4 min | 1 |
| 94° C. 30 s | 25 |
| 58° C. 30 s | |
| 72° C. 2 min | |
| 72° C. 5 min | 1 |
| 4° C. | 1 |

(2) A PCR solution obtained in step (1) was subjected to 1% agarose gel electrophoresis, and gel was cut, recovered and purified to obtain a PCR amplification product.

(3) The Gibson Assembly® Master Mix kit was used for ligating a PCR purified product obtained in step (2) and the codon-optimized lacZα gene obtained in Example 1. A ligation system is shown in Table 3.

TABLE 3

| PCR amplification product | About 200 ng, 5 μL |
|---|---|
| lacZα gene | About 120 ng, 5 μL |
| Gibson Assembly ® Master Mix | 10 μL |
| Sterilized and deionized H₂O | 0 μL |

A ligation condition was a ligation reaction of 1 h at 50° C.

(4) A ligation product obtained in step (3) was transformed into Top10F' competent cells which were finally coated with a kanamycin-resistant LB plate containing IPTG and X-gal and cultivated overnight at 37° C. A blue single clone was picked and subjected to Sanger sequencing on the next day, and a plasmid with a correct sequence was reserved and named pUC57-lacZ.

(II) A sequence, 5'-CTTTATGCTTCCGGCTCG-3' (SEQ ID NO: 2), between −35 region and −10 region in a promoter region of the β-galactosidase of the pUC57-lacZ plasmid was mutated into a sequence recognizable by the endonuclease, which specifically includes steps described below.

(1) The pUC57-lacZ plasmid successfully constructed in step (I) was used as a template, and primers F1-EcoRV, R1-EcoRV, F2-EcoRV, R2-EcoRV, F3-EcoRV, R3-EcoRV, F4-EcoRV, R4-EcoRV, F5-EcoRV, R5-EcoRV, F6-AleI, R6-AleI, F7-BamHI-XhoI and R7-BamHI-XhoI (SEQ ID NO: 15-SEQ ID NO: 28) were used as primers for the PCR amplification. Specific sequences are listed in Table 4.

TABLE 4

| NO. | Sequence |
|---|---|
| SEQ ID NO. 15 (F1-EcoRV) | CCGGAAGCGATATCTGTAAAG CCTGGGGTGCCTAATGAGTG |
| SEQ ID NO. 16 (R1-EcoRV) | CCCCAGGCTTTACAGATATCGCTT CCGGCTCGTATGTTGTGTGGAATT |
| SEQ ID NO. 17 (F2-EcoRV) | GAGCCGGAGATATCAAGTGTAAAG CCTGGGGTGCCTAATGAG |

TABLE 4-continued

| NO. | Sequence |
|-----|----------|
| SEQ ID NO. 18 (R2-EcoRV) | CAGGCTTTACACTTGATATCTCCGG CTCGTATGTTGTGTGGAATTGTG |
| SEQ ID NO. 19 (F3-EcoRV) | TACGAGCCGATATCATAAAGTGTAAA GCCTGGGGTGCCTAAT |
| SEQ ID NO. 20 (R3-EcoRV) | GCTTTACACTTTATGATATCGGCTCG TATGTTGTGTGGAATTGTGAGC |
| SEQ ID NO 21 (F4-EcoRV) | ACATACGAGATATCAGCATAAAGTGT AAAGCCTGGGGTGCCT |
| SEQ ID NO. 22 (R4-EcoRV) | TTACACTTTATGCTGATATCTCGTATG TTGTGTGGAATTGTGAGCGGA |
| SEQ ID NO. 23 (F5-EcoRV) | ACAACATAGATATCGGAAGCATAAAGT GTAAAGCCTGGGGTG |
| SEQ ID NO. 24 (R5-EcoRV) | CACTTTATGCTTCCGATATCTATGTTG TGTGGAATTGTGAGCGGATAA |
| SEQ ID NO. 25 (F6-AleI) | AACATACGAGCACGAAGGTGAAAGTGT AAAGCCTGGGGTGCCTAATGA |
| SEQ ID NO. 26 (R6-AleI) | TACACTTTCACCTTCGTGCTCGTATGT TGTGTGGAATTGTGAGCGG |
| SEQ ID NO. 27 (F7-BamHI-XhoI) | CATAGGATCCGATATCCTCGAGTGTA AAGCCTGGGGTGCCTAATGAGTGA |
| SEQ ID NO. 28 (R7-BamHI-XhoI) | TACACTCGAGGATATCGGATCCTATGT TGTGTGGAATTGTGAGCGGATAA |

A specific PCR system is shown in Table 1, and reaction conditions are listed in Table 2.

(2) A PCR solution obtained in step (1) was subjected to 1% agarose gel electrophoresis, and gel was cut, recovered and purified to obtain a PCR amplification product. The Gibson Assembly® Master Mix kit was used for a ligation reaction. A ligation system is shown in Table 5.

TABLE 5

| | |
|---|---|
| PCR amplification product | About 300 ng, 10 μL |
| Gibson Assembly ® Master Mix | 10 μL |
| Sterilized and deionized H₂O | 0 μL |

A ligation condition was a ligation reaction of 1 h at 50° C.

(3) Each ligation product obtained in step (2) was transformed into Top10F' competent cells which were finally coated with a kanamycin-resistant LB plate containing IPTG and X-gal and cultivated overnight at 37° C. A blue single clone was picked and subjected to Sanger sequencing on the next day, and a plasmid with a correct sequence was reserved and separately named pUC57-lacZ-Mu-1 (5'-CTT-TATGCTTCCGGCTCG-3' (SEQ ID NO: 2) was mutated into 5'-GATATCGCTTCCGGCTCG-3' (SEQ ID NO: 3), and the plasmid was constructed with primers F1-EcoRV+ R1-EcoRV), pUC57-lacZ-Mu-2 (5'-CTT-TATGCTTCCGGCTCG-3' (SEQ ID NO: 2) was mutated into 5'-CTTGATATCTCCGGCTCG-3' (SEQ ID NO: 4), and the plasmid was constructed with primers F2-EcoRV+R2-EcoRV), pUC57-lacZ-Mu-3 (5'-CTT-TATGCTTCCGGCTCG-3' (SEQ ID NO: 2) was mutated into 5'-CTTTATGATATCGGCTCG-3' (SEQ ID NO: 5), and the plasmid was constructed with primers F3-EcoRV+R3-EcoRV), pUC57-lacZ-Mu-4 (5'-CTT-TATGCTTCCGGCTCG-3' (SEQ ID NO: 2) was mutated into 5'-CTTTATGCTGATATCTCG-3' (SEQ ID NO: 6), and the plasmid was constructed with primers F4-EcoRV+R4-EcoRV), pUC57-lacZ-Mu-5 (5'-CTT-TATGCTTCCGGCTCG-3' (SEQ ID NO: 2) was mutated into 5'-CTTTATGCTTCCGATATC-3' (SEQ ID NO: 7), and the plasmid was constructed with primers F5-EcoRV+R5-EcoRV), pUC57-lacZ-Mu-6 (5'-CTT-TATGCTTCCGGCTCG-3' (SEQ ID NO: 2) was mutated into 5'-CTTTCACCTTCGTGCTCG-3' (SEQ ID NO: 8), and the plasmid was constructed with primers F6-AleI+R6-AleI), and pUC57-lacZ-Mu-7 (5'-CTT-TATGCTTCCGGCTCG-3' (SEQ ID NO: 2) was mutated into 5'-CTCGAGGATATCGGATCC-3' (SEQ ID NO: 9), and the plasmid was constructed with primers F7-BamHI-XhoI+R7-BamHI-XhoI).

(III) Vector Cloning Experiments (1) The correct plasmids pUC57-lacZ-Mu-1, pUC57-lacZ-Mu-2, pUC57-lacZ-Mu-3, pUC57-lacZ-Mu-4, pUC57-lacZ-Mu-5 constructed in step (II) were digested with a restriction enzyme EcoRV, pUC57-lacZ-Mu-6 was digested with a restriction enzyme AleI, and pUC57-lacZ-Mu-7 was digested with restriction enzymes BamHI and XhoI. Digestion products were subjected to 1% agarose gel electrophoresis, and gel was cut, recovered and purified.

(2) Reversely complementary primers of 24 bp and 48 bp were synthesized and annealed to form double-stranded DNA. Nucleotide sequences of the reversely complementary primers of 24 bp and 48 bp are shown by SEQ ID NO: 43-SEQ ID NO: 46, specifically:

```
SEQ ID NO. 43:
TTCATACAGCAGGCTATGTTTAGG;

SEQ ID NO. 44:
CCTAAACATAGCCTGCTGTATGAA;

SEQ ID NO. 45:
TAAGCCGATACTGTATTTTTTATCCATAGCTGTTTCCTGTGTGAAATT;

SEQ ID NO. 46:
AATTTCACACAGGAAACAGCTATGGATAAAAAATACAGTATCGGCTTA.
```

(3) \ DNA was used as a template, and F-ADNA-200 bp+R-ADNA-200 bp were used as primers for the PCR amplification. Nucleotide sequences of the primers F-ADNA-200 bp and R-ADNA-200 bp are shown by SEQ ID NO: 47-SEQ ID NO: 48, specifically:

SEQ ID NO. 47 (F-λDNA-200bp):
AATGGTCAGGATCCGTTGAATGGGCGGATGCTAATTACTATCTCCCG;

SEQ ID NO. 48 (R-λDNA-200bp):
TGAAGAACCTCGAGTTATGCTCTATAAAGTAGGCATAAACACCCAGC.

A PCR system is shown in Table 1, and a PCR amplification program is shown in Table 6.

TABLE 6

| Amplification program | |
| --- | --- |
| Reaction Program | Number of Cycles |
| 95° C. 4 min | 1 |
| 94° C. 30 s | 25 |
| 58° C. 30 s | |
| 72° C. 15 s | |
| 72° C. 3 min | 1 |
| 4° C. | 1 |

(4) A PCR solution obtained in step (3) was subjected to 1% agarose gel electrophoresis, and gel was cut, recovered and purified to obtain a PCR amplification product. The purified PCR amplification product was digested with BamHI and XhoI. A digestion system is shown in Table 7.

TABLE 7

| PCR amplification product | About 900 ng, 12 μL |
| --- | --- |
| BamHI | 1 μL |
| XhoI | 1 μL |
| 10 × buffer | 2 μL |
| Sterilized and deionized $H_2O$ | 4 μL |

A digestion condition was digestion of 1 h at 37° C., and the digestion product was recovered and purified using an Axygen purification kit.

(5) Fragments of 24 bp and 48 bp formed after annealing in step (2) were ligated to the digested and purified vectors in step (1), pUC57-lacZ-Mu-1, pUC57-lacZ-Mu-2, pUC57-lacZ-Mu-3, pUC57-lacZ-Mu-4, pUC57-lacZ-Mu-5 and pUC57-lacZ-Mu-6 separately, and the purified digestion product in step (4) was ligated to the digested and purified vector in step (1), pUC57-lacZ-Mu-7. A ligation system is shown in Table 8.

TABLE 8

| Foreign DNA | About 90 ng, 3 μL |
| --- | --- |
| Digested vector | About 30 ng, 1 μL |
| 10 × buffer | 1 μL |
| T4 DNA ligase | 1 μL |
| Sterilized and deionized $H_2O$ | 4 μL |

A ligation condition was a ligation reaction of 1 h at 22° C.

(6) Each ligation product obtained in step (5) was transformed into Top10F' competent cells which were finally coated with the kanamycin-resistant LB plate containing IPTG and X-gal and cultivated overnight at 37° C. 24 white single clones were picked on the plate of the cloned DNA fragment of about 200 bp (pUC57-lacZ-Mu-7 vector) for colony PCR identification on the next day. The PCR system is shown in Table 9.

TABLE 9

| PCR system | |
| --- | --- |
| Bacterium solution template | 3 μL |
| F-λDNA-200 bp | 10 pM, 0.5 μL |
| R-λDNA-200 bp | 10 pM, 0.5 μL |
| dNTP | 5 mM each, 0.5 μL |
| 10 × Taq buffer | 5 μL |
| Taq DNA polymerase | 5 U/μL, 0.5 μL |
| $H_2O$ | 40 μL |

A PCR amplification program is shown in Table 10.

TABLE 10

| Amplification program | |
| --- | --- |
| Reaction Program | Number of Cycles |
| 95° C. 6 min | 1 |
| 94° C. 30 s | 25 |
| 58° C. 30 s | |
| 72° C. 15 s | |
| 72° C. 3 min | 1 |
| 4° C. | 1 |

A PCR identification result is shown in FIG. 1.

The result in FIG. 1 shows that all clones are positive clones. 12 clones were randomly selected from the 24 clones that were positive after colony identification and meanwhile, 12 white single clones were selected from the plates of foreign DNA fragments of 24 bp and 48 bp separately and subjected to Sanger sequencing. Sequencing results show that all clones have correct sequences. Experimental results show that the vector of the present application may be used for cloning foreign DNA of 24 bp or more.

Example 3 Construction of Three Mutant Plasmids of pUC57-lacZ-Mu-2

A method for constructing the pUC57-lacZ-Mu-2 plasmid includes steps described below.

(1) The plasmid pUC57-lacZ-Mu-2 constructed in Example 2 was used as a template, and F1-del+R1-del, F2-del+R2-del and F3-del+R3-del were used as primers for PCR amplification. Nucleotide sequences of the primers F1-del, R1-del, F2-del, R2-del, F3-del and R3-del are shown by SEQ ID NO: 49-SEQ ID NO: 54, specifically:

SEQ ID NO. 49 (F1-del):
ATACGAGCCGGAGAATCAAGTGTAAAGCCTGGGGTGCCTAAT;

SEQ ID NO. 50 (R1-del):
GCTTTACACTTGATTCTCCGGCTCGTATGTTGTGTGGAATTG;

SEQ ID NO. 51 (F2-del):
TACGAGCCGGAGATTCAAGTGTAAAGCCTGGGGTGCCTAATG;

SEQ ID NO. 52 (R2-del):
GGCTTTACACTTGAATCTCCGGCTCGTATGTTGTGTGGAATTG;

SEQ ID NO. 53 (F3-del):
ATACGAGCCGGAGATCAAGTGTAAAGCCTGGGGTGCCTAATG;

SEQ ID NO. 54 (R4-del):
GGCTTTACACTTGATCTCCGGCTCGTATGTTGTGTGGAATTG.

A PCR system is shown in Table 1 in Example 2, and a PCR amplification program is shown in Table 2 in Example 2.

(2) A PCR solution obtained in step (1) was subjected to 1% agarose gel electrophoresis, and gel was cut, recovered and purified to obtain a PCR amplification product. The Gibson Assembly® Master Mix (NEB) kit was used for a ligation reaction. A ligation system is shown in Table 5 in Example 2.

A ligation condition was a ligation reaction of 1 h at 50° C.

(3) Each ligation product obtained in step (2) was transformed into Top10F' competent cells which were finally coated with a kanamycin-resistant LB plate containing IPTG and X-gal and cultivated overnight at 37° C. Blue single clones were picked and subjected to Sanger sequencing on the next day, and plasmids with correct sequences were reserved to obtain the three mutant plasmids of the pUC57-lacZ-Mu-2, which are named pUC57-lacZ-Mu-2A, pUC57-lacZ-Mu-2B and pUC57-lacZ-Mu-2C, separately.

An EcoRV site of pUC57-lacZ-Mu-2A was mutated into GATTC, that is, the sequence was mutated from 5'-CTT-GATATCTCCGGCTCG-3' (SEQ ID NO: 59) to 5'-CTT-GATTCTCCGGCTCG-3' (SEQ ID NO: 60). An EcoRV site of pUC57-lacZ-Mu-2B was mutated into GAATC, that is, the sequence was mutated from 5'-CTTGA-TATCTCCGGCTCG-3' (SEQ ID NO: 59) to 5'-CTT-GAATCTCCGGCTCG-3' (SEQ ID NO: 61). An EcoRV site of pUC57-lacZ-Mu-2C was mutated into GATC, that is, the sequence was mutated from 5'-CTTGA-TATCTCCGGCTCG-3' (SEQ ID NO: 59) to 5'-CTT-GATCTCCGGCTCG-3' (SEQ ID NO: 62).

(4) Correct plasmids pUC57-lacZ-Mu-2A, pUC57-lacZ-Mu-2B and pUC57-lacZ-Mu-2C in step (3) each were transformed into Top10F' competent cells which were finally coated with the kanamycin-resistant LB plate containing IPTG and X-gal and cultivated overnight at 37° C. It was found on the next day that colonies on three plates were all blue. 5 single clones were selected from each plate and subjected to Sanger sequencing. Sequencing results show that all clones have correct sequences.

Experimental results show that β-galactosidase promoters of the three mutant plasmids of pUC57-lacZ-Mu-2 (pUC57-lacZ-Mu-2A, pUC57-lacZ-Mu-2B and pUC57-lacZ-Mu-2C) still have activity and can express lacZα and make colonies appear blue when induced by IPTG. Meanwhile, the experimental results show that the linearized pUC57-lacZ-Mu-2 vector after EcoRV digestion can still express lacZα and make colonies appear blue after the self-ligation of the linearized vector that lacks 1 base at one end of the site (pUC57-lacZ-Mu-2A and pUC57-lacZ-Mu-2B plasmids) or two ends of the site (pUC57-lacZ-Mu-2C plasmid), that is, the vector of the present application, after digested by the endonuclease, will not generate false positive clones due to the self-ligation for the lack of 1 base at one end or two ends of the site.

Example 4 Construction and Function Verification of a Low-Copy Cloning Vector

A method for constructing the low-copy cloning vector includes specific steps described below.

(I) The lacZα gene of pCK plasmid was replaced with the optimized lacZα gene in Example 1, specifically including steps described below.

(1) The pCK plasmid was used as a template and SEQ ID NOs: 55-56 were used as primers for PCR amplification. Specific sequences are as follows:

```
SEQ ID NO. 55 (forward
primer):
ATGCAGGCTCGGTTCCAGCATGGTCATA

GCTGTTTCCTGTGTGAAATTGTTATCC;

SEQ ID NO. 56 (reverse
primer):
AGCACCATTTGCAGCGATGCCGCCTAAT

TAAGCCAGCCCCGAGTAGCTAGACAGG.
```

A PCR system is shown in Table 1 in Example 2, and reaction conditions are shown in Table 2 in Example 2.

(2) A PCR solution obtained in step (1) was subjected to 1% agarose gel electrophoresis, and gel was cut, recovered and purified to obtain a PCR amplification product.

(3) The Gibson Assembly® Master Mix kit was used for ligating a PCR purified product obtained in step (2) and the codon-optimized lacZα gene obtained in Example 1. A ligation system is shown in Table 3 in Example 2.

A ligation condition was a ligation reaction of 1 h at 50° C.

(4) A ligation product obtained in step (3) was transformed into Top10F' competent cells which were finally coated with a kanamycin-resistant LB plate containing IPTG and X-gal and cultivated overnight at 37° C. A blue single clone was picked and subjected to Sanger sequencing on the next day, and a plasmid with a correct sequence was reserved and named pCK-lacZ.

(II) A sequence, 5'-CTTTATGCTTCCGGCTCG-3' (SEQ ID NO: 2), between −35 region and −10 region in a promoter region of the β-galactosidase of the pCK-lacZ plasmid was mutated into a sequence recognizable by the endonuclease, which specifically includes steps described below.

(1) The pCK-lacZ plasmid successfully constructed in step (I) was used as a template, and primers F1-EcoRV, R1-EcoRV, F2-EcoRV, R2-EcoRV, F3-EcoRV, R3-EcoRV, F4-EcoRV, R4-EcoRV, F5-EcoRV, R5-EcoRV, F6-AleI, R6-AleI, F7-BamHI-XhoI and R7-BamHI-XhoI (SEQ ID NO: 15-SEQ ID NO: 28) were used as primers for the PCR amplification. Specific sequences are listed in Table 4 in Example 2. A specific PCR system is shown in Table 1 in Example 2, and reaction conditions are shown in Table 2 in Example 2.

(2) A PCR solution obtained in step (1) was subjected to 1% agarose gel electrophoresis, and gel was cut, recovered and purified to obtain a PCR amplification product. The Gibson Assembly® Master Mix kit was used for a ligation reaction. A ligation system is shown in Table 5 in Example 2.

A ligation condition was a ligation reaction of 1 h at 50° C.

(3) Each ligation product obtained in step (2) was transformed into Top10F' competent cells which were finally coated with the kanamycin-resistant LB plate containing IPTG and X-gal and cultivated overnight at 37° C. A blue single clone was picked and subjected to Sanger sequencing on the next day, and a plasmid with a correct sequence was reserved and separately named pCK-lacZ-Mu-1 (5'-CTT-TATGCTTCCGGCTCG-3' (SEQ ID NO: 2) was mutated into 5'-GATATCGCTTCCGGCTCG-3' (SEQ ID NO: 3), and the plasmid was constructed with primers F1-EcoRV+ R1-EcoRV), pCK-lacZ-Mu-2 (5'-CTT-TATGCTTCCGGCTCG-3' (SEQ ID NO: 2) was mutated into 5'-CTTGATATCTCCGGCTCG-3' (SEQ ID NO: 4), and the plasmid was constructed with primers F2-EcoRV+R2-EcoRV), pCK-lacZ-Mu-3 (5'-CTTTATGCTTCCGGCTCG- 3' (SEQ ID NO: 2) was mutated into 5'-CTTTATGA-TATCGGCTCG-3' (SEQ ID NO: 5), and the plasmid was constructed with primers F3-EcoRV+R3-EcoRV), pCK-lacZ-Mu-4 (5'-CTTTATGCTTCCGGCTCG-3' (SEQ ID NO: 2) was mutated into 5'-CTTTATGCTGATATCTCG-3' (SEQ ID NO: 6), and the plasmid was constructed with primers F4-EcoRV+R4-EcoRV), pCK-lacZ-Mu-5 (5'-CTT-TATGCTTCCGGCTCG-3' (SEQ ID NO: 2) was mutated into 5'-CTTTATGCTTCCGATATC-3' (SEQ ID NO: 7), and the plasmid was constructed with primers F5-EcoRV+R5-EcoRV), pCK-lacZ-Mu-6 (5'-CTTTATGCTTCCGGCTCG-3' (SEQ ID NO: 2) was mutated into 5'-CTTT-CACCTTCGTGCTCG-3' (SEQ ID NO: 8), and the plasmid was constructed with primers F6-AleI+R6-AleI), and pCK-lacZ-Mu-7 (5'-CTTTATGCTTCCGGCTCG-3' (SEQ ID NO: 2) was mutated into 5'-CTCGAGGATATCGGATCC-3' (SEQ ID NO: 9), and the plasmid was constructed with primers F7-BamHI-XhoI+R7-BamHI-XhoI).

(III) Vector Cloning Experiments (1) The correct plasmids pCK-lacZ-Mu-1, pCK-lacZ-Mu-2, pCK-lacZ-Mu-3, pCK-lacZ-Mu-4 and pCK-lacZ-Mu-5 constructed in step (II) were digested with a restriction enzyme EcoRV, pCK-lacZ-Mu-6 was digested with a restriction enzyme AleI, and pCK-lacZ-Mu-7 was digested with restriction enzymes BamHI and XhoI. Digestion products were subjected to 1% agarose gel electrophoresis, and gel was cut, recovered and purified.

(2) Reversely complementary primers of 24 bp and 48 bp were synthesized and annealed to form double-stranded DNA. Nucleotide sequences of the reversely complementary primers of 24 bp and 48 bp are shown by SEQ ID NO: 43-SEQ ID NO: 46 in Example 2.

(3) \ DNA was used as a template, and F-ADNA-200 bp+R-ADNA-200 bp were used as primers for the PCR amplification. Nucleotide sequences of the primers F-ADNA-200 bp and R-ADNA-200 bp are shown by SEQ ID NO: 47-SEQ ID NO: 48 in Example 2.

A PCR system is shown in Table 1 in Example 2, and a PCR amplification program is shown in Table 6 in Example 2.

(4) A PCR solution obtained in step (3) was subjected to 1% agarose gel electrophoresis, and gel was cut, recovered and purified to obtain a PCR amplification product. The purified PCR amplification product was digested with BamHI and XhoI. A digestion system is shown in Table 7 in Example 2.

A digestion condition was digestion of 1 h at 37° C., and the digestion product was recovered and purified using an Axygen purification kit.

(5) Fragments of 24 bp and 48 bp formed after annealing in step (2) were ligated to the digested and purified vectors in step (1), pCK-lacZ-Mu-1, pCK-lacZ-Mu-2, pCK-lacZ-Mu-3, pCK-lacZ-Mu-4, pCK-lacZ-Mu-5 and pCK-lacZ-Mu-6, separately, and the purified digestion product in step (4) was ligated to the digested and purified vector in step (1), pCK-lacZ-Mu-7. A ligation system is shown in Table 8 in Example 2.

A ligation condition was a ligation reaction of 1 h at 22° C.

(6) Each ligation product obtained in step (5) was transformed into Top10F' competent cells which were finally coated with the kanamycin-resistant LB plate containing IPTG and X-gal and cultivated overnight at 37° C. 12 white single clones were picked on the plate of the cloned DNA fragment of about 200 bp (pCK-lacZ-Mu-7 vector) for colony PCR identification on the next day. The PCR system is shown in Table 9.

A PCR amplification program is shown in Table 10.

Figure 2:
FIG. 2 is an electrophoresis diagram of colony PCR identification in Example 4 of the present application, where a size of a DNA marker is 0.1 kb, 0.25 kb, 0.5 kb, 0.75 kb, 1 kb, 1.5 kb, 2 kb, 3 kb and 5 kb.

A result in FIG. 2 shows that all clones are positive clones. 12 white single clones selected from each of other plates and 12 single clones that were all positive after colony identification were subjected to Sanger sequencing. Sequencing results show that all clones have correct sequences. Experimental results show that the vector of the present application may be used for cloning foreign DNA of 24 bp or more.

Example 5 Construction and Function Verification of a Single-Copy Cloning Vector A method for constructing the single-copy cloning vector includes specific steps described below.

(I) The lacZα gene of pCC1 plasmid was replaced with the optimized lacZα gene in Example 1, specifically including steps described below.

(1) The pCC1 plasmid was used as a template and SEQ ID NOs: 57-58 were used as primers for PCR amplification. Specific sequences are as follows:

```
SEQ ID NO. 57 (forward
primer):
ATGCAGGCTCGGTTCCAGCATGGTCATAG

CTGTTTCCTGTGTGAAATTGTTATCC;

SEQ ID NO. 58 (reverse
primer):
AGCACCATTTGCAGCGATGCCGCCTAATT

AAGCCAGCCCCGACACCCGCCAACAC.
```

A PCR system is shown in Table 1 in Example 2, and reaction conditions are shown in Table 11.

TABLE 11

| Amplification program | |
|---|---|
| Reaction Program | Number of Cycles |
| 95° C. 4 min | 1 |
| 94° C. 30 s | 25 |
| 58° C. 30 s | |
| 72° C. 5 min | |
| 72° C. 8 min | 1 |
| 4° C. | 1 |

(2) A PCR solution obtained in step (1) was subjected to 1% agarose gel electrophoresis, and gel was cut, recovered and purified to obtain a PCR amplification product.

(3) The Gibson Assembly® Master Mix kit was used for ligating a PCR purified product obtained in step (3) and the codon-optimized lacZα gene obtained in Example 1. A ligation system is shown in Table 12 in Example 2.

TABLE 12

| PCR amplification product | About 387 ng, 9 μL |
|---|---|
| lacZα gene | About 100 ng, 1 μL |
| Gibson Assembly ® Master Mix | 10 μL |
| Sterilized and deionized H₂O | 0 μL |

A ligation condition was a ligation reaction of 1 h at 50° C.

(4) A ligation product obtained in step (3) was transformed into Top10F' competent cells which were finally coated with a chloramphenicol-resistant LB plate containing IPTG and X-gal and cultivated overnight at 37° C. A blue single clone was picked and subjected to Sanger sequencing on the next day, and a plasmid with a correct sequence was reserved and named pCC1-lacZ.

(II) A sequence, 5'-CTTTATGCTTCCGGCTCG-3' (SEQ ID NO: 2), between −35 region and −10 region in a promoter region of the β-galactosidase of the pCC1-lacZ plasmid was mutated into a sequence recognizable by the endonuclease, which specifically includes steps described below.

(1) The pCC1-lacZ plasmid successfully constructed in step (I) was used as a template, and primers F1-PmlI+R1-PmlI, F2-PmlI+R2-PmlI, F3-PmlI+R3-PmlI, F4-PmlI+R4-PmlI, F5-PmlI+R5-PmlI and F7-BamHI-XhoI+R7-BamHI-XhoI (SEQ ID NO: 29-SEQ ID NO: 38, SEQ ID NO: 27-SEQ ID NO: 28) were used as primers for the PCR amplification. Specific sequences are listed in Table 13.

TABLE 13

| NO. | Sequence |
| --- | --- |
| SEQ ID NO. 29 (F1-PmlI) | CCGGAAGCCACGTGTGTAAAGC CTGGGGTGCCTAATGAGTG |
| SEQ ID NO. 30 (R1-PmlI) | CCCCAGGCTTTACACACGTGGCTT CCGGCTCGTATGTTGTGTGGAATT |
| SEQ ID NO. 31 (F2-PmlI) | GAGCCGGACACGTGAAGTGTA AAGCCTGGGGTGCCTAATGAG |
| SEQ ID NO. 32 (R2-PmlI) | CAGGCTTTACACTTCACGTGTCCG GCTCGTATGTTGTGTGGAATTGTG |
| SEQ ID NO. 33 (F3-PmlI) | TACGAGCCCACGTGATAAAGTGT AAAGCCTGGGGTGCCTAAT |
| SEQ ID NO. 34 (R3-PmlI) | GCTTTACACTTTATCACGTGGGCT CGTATGTTGTGTGGAATTGTGAGC |
| SEQ ID NO. 35 (F4-PmlI) | ACATACGACACGTGAGCATAA AGTGTAAAGCCTGGGGTGCCT |
| SEQ ID NO. 36 (R4-PmlI) | TTACACTTTATGCTCACGTGTCGT ATGTTGTGTGGAATTGTGAGCGGA |
| SEQ ID NO. 37 (F5-PmlI) | ACAACATACACGTGGGAAGCA TAAAGTGTAAAGCCTGGGGTG |
| SEQ ID NO. 38 (R5-PmlI) | CACTTTATGCTTCCCACGTGTATG TTGTGTGGAATTGTGAGCGGATAA |

TABLE 13 -continued

| NO. | Sequence |
| --- | --- |
| SEQ ID NO. 27 (F7-BamHI-XhoI) | CATAGGATCCGATATCCTCGAGTGT AAAGCCTGGGGTGCCTAATGAGTGA |
| SEQ ID NO. 28 (R7-BamHI-XhoI) | TACACTCGAGGATATCGGATCCTATG TTGTGTGGAATTGTGAGCGGATAA |

A specific PCR system is shown in Table 1 in Example 2, and reaction conditions are shown in Table 11.

(2) A PCR solution obtained in step (1) was subjected to 1% agarose gel electrophoresis, and gel was cut, recovered and purified to obtain a PCR amplification product. The Gibson Assembly® Master Mix kit was used for a ligation reaction. A ligation system is shown in Table 14 in Example 2.

TABLE 14

| PCR amplification product | About 490 ng, 10 μL |
| --- | --- |
| Gibson Assembly ® Master Mix | 10 μL |
| Sterilized and deionized H$_2$O | 0 μL |

A ligation condition was a ligation reaction of 1 h at 50° C.

(3) Each ligation product obtained in step (2) was transformed into Top10F' competent cells which were finally coated with the chloramphenicol-resistant LB plate containing IPTG and X-gal and cultivated overnight at 37° C. A blue single clone was picked and subjected to Sanger sequencing on the next day, and a plasmid with a correct sequence was reserved and separately named pCC1-lacZ-Mu-1 (5'-CTTTATGCTTCCGGCTCG-3' (SEQ ID NO: 2) was mutated into 5'-CACGTGGCTTCCGGCTCG-3' (SEQ ID NO: 10), and the plasmid was constructed with primers F1-PmlI+R1-PmlI), pCC1-lacZ-Mu-2 (5'-CTT-TATGCTTCCGGCTCG-3' (SEQ ID NO: 2) was mutated into 5'-CTTCACGTGTCCGGCTCG-3' (SEQ ID NO: 11), and the plasmid was constructed with primers F2-PmlI+R2-PmlI), pCC1-lacZ-Mu-3 (5'-CTTTATGCTTCCGGCTCG-3' (SEQ ID NO: 2) was mutated into 5'-CTTTAT-CACGTGGGCTCG-3' (SEQ ID NO: 12), and the plasmid was constructed with primers F3-PmlI+R3-PmlI), pCC1-lacZ-Mu-4 (5'-CTTTATGCTTCCGGCTCG-3' (SEQ ID NO: 2) was mutated into 5'-CTTTATGCTCACGTGTCG-3' (SEQ ID NO: 13), and the plasmid was constructed with primers F4-PmlI+R4-PmlI), pCC1-lacZ-Mu-5 (5'-CTT-TATGCTTCCGGCTCG-3' (SEQ ID NO: 2) was mutated into 5'-CTTTATGCTTCCCACGTG-3' (SEQ ID NO: 14), and the plasmid was constructed with primers F5-PmlI+R5-PmlI), and pCC1-lacZ-Mu-6 (5'-CTT-TATGCTTCCGGCTCG-3' (SEQ ID NO: 2) was mutated into 5'-CTCGAGGATATCGGATCC-3' (SEQ ID NO: 9), and the plasmid was constructed with primers F7-BamHI-XhoI+R7-BamHI-XhoI).

(III) Vector Cloning Experiments (1) The correct plasmids pCC1-lacZ-Mu-1, CC1-lacZ-Mu-2, pCC1-lacZ-Mu-3, pCC1-lacZ-Mu-4 and pCC1-lacZ-Mu-5 constructed in step (II) were digested with a restriction enzyme PmlI, and pCC1-lacZ-Mu-6 was digested with restriction enzymes BamHI and XhoI. Digestion products were subjected to 1% agarose gel electrophoresis, and gel was cut, recovered and purified.

(2) Reversely complementary primers of 24 bp and 48 bp were synthesized and annealed to form double-stranded DNA. Nucleotide sequences of the reversely complementary primers of 24 bp and 48 bp are shown by SEQ ID NO: 43-SEQ ID NO: 46 in Example 2.

(3) 2 DNA was used as a template, and F-ADNA-200 bp+R-ADNA-200 bp were used as primers for the PCR amplification. Nucleotide sequences of the primers F-ADNA-200 bp and R-ADNA-200 bp are shown by SEQ ID NO: 47-SEQ ID NO: 48 in Example 2.

A PCR system is shown in Table 1, and a PCR amplification program is shown in Table 6.

(4) A PCR solution obtained in step (3) was subjected to 1% agarose gel electrophoresis, and gel was cut, recovered and purified to obtain a PCR amplification product. The purified PCR amplification product was digested with BamHI and XhoI. A digestion system is shown in Table 7 in Example 2.

A digestion condition was digestion of 1 h at 37° C., and the digestion product was recovered and purified using an Axygen purification kit.

(5) Fragments of 24 bp and 48 bp formed after annealing in step (2) were ligated to the digested and purified vectors in step (1), pCC1-lacZ-Mu-1, pCC1-lacZ-Mu-2, pCC1-lacZ-Mu-3, pCC1-lacZ-Mu-4 and pCC1-lacZ-Mu-5, separately, and the purified digestion product in step (4) was ligated to the digested and purified vector in step (1), pCC1-lacZ-Mu-6. A ligation system is shown in Table 7 in Example 2.

A ligation condition was a ligation reaction of 1 h at 22° C.

(6) Each ligation product obtained in step (5) was transformed into Top10F' competent cells which were finally coated with the chloramphenicol-resistant LB plate containing IPTG and X-gal and cultivated overnight at 37° C. 24 white single clones were picked on the plate of the cloned DNA fragment of about 200 bp (pCC1-lacZ-Mu-6 vector) for colony PCR identification on the next day. The PCR system is shown in Table 9.

A PCR amplification program is shown in Table 10. A result is shown in FIG. 3.

Figure 3:
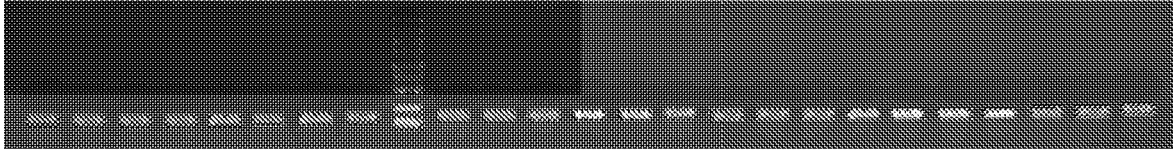
FIG. 3 is an electrophoresis diagram of colony PCR identification in Example 5 of the present application, where a size of a DNA marker is 0.1 kb, 0.25 kb, 0.5 kb, 0.75 kb, 1 kb, 1.5 kb, 2 kb, 3 kb and 5 kb.

An electrophoresis result in FIG. 3 shows that all clones are positive clones. 12 clones were randomly selected from the 24 clones that were positive after colony identification and meanwhile, 12 white single clones were selected from the plates of foreign DNA fragments of 24 bp and 48 bp separately and subjected to Sanger sequencing. Sequencing results show that all clones have correct sequences. Experimental results show that the vector of the present application may be used for cloning foreign DNA of 24 bp or more.

To conclude, in the present application, a sequence between −35 region and −10 region in a strong promoter region of the β-galactosidase is mutated into sites that can be recognized and digested by the endonuclease, and during cloning, a vector is digested with an appropriate endonuclease or a linearized vector is prepared by a PCR method, and then the linearized vector is ligated to foreign genes, so that a strong promoter of the β-galactosidase has significantly decreased activity due to the insertion of a foreign DNA fragment, an expression amount of the lacZα gene is significantly reduced, and a colony containing a recombinant plasmid is white. By use of the above-mentioned method, the present application overcomes the common problem that a strong promoter in a vector based on blue-white screening initiates the transcription or translation of foreign genes and a transcription or translation product might be toxic to a host and cannot be cloned, can avoid the deficiency that frameshift mutation of the lacZα gene due to a lack of 1-2 bp of the vector at digestion sites results in false positive clones, and can eliminate a false negative phenomenon that a plate is rich in blue spots due to a small fragment of foreign DNA and a reading frame of the lacZα gene which is unchanged by inserting the foreign DNA.

The applicant has stated that although the detailed method of the present application is described through the examples described above, the present application is not limited to the detailed method described above, which means that implementation of the present application does not necessarily depend on the detailed method described above. It should be apparent to those skilled in the art that any improvements made to the present application, equivalent replacements of raw materials of the product of the present application, additions of adjuvant ingredients to the product of the present application, and selections of specific manners, etc., all fall within the protection scope and the disclosed scope of the present application.

What is claimed is:

1. A β-galactosidase promoter, consisting of a –35 region, a –10 region, and a mutated nucleic acid sequence between the –35 region and the –10 region, wherein:

the mutated nucleic acid sequence comprises at least one recognition site for an endonuclease, each recognition site for an endonuclease selected from the group consisting of EcoRV, AleI, BamHI, XhoI, and PmlI;

the –35 region has a nucleic acid sequence of 5'-TT-TACA-3';

a 5' end of the mutated nucleic acid sequence is linked to a 3' end of the –35 region;

a 3' end of the mutated nucleic acid sequence is linked to a 5' end of the –10 region; and the mutated nucleic acid sequence is 16 to 18 base pairs in length.

2. The promoter of claim 1, wherein the mutated nucleic acid sequence between the –35 region and the –10 region of the promoter is SEQ ID NO: 4.

3. A vector, comprising the promoter of claim 1 and a reporter gene regulated by the promoter.

4. The vector of claim 3, wherein insertion of a foreign DNA at the recognition site for the endonuclease significantly reduces activity of the promoter.

5. The vector of claim 3, wherein the vector is a cloning vector or an expression vector.

6. An isolated host cell, comprising the vector of claim 3.

7. The host cell of claim 6, wherein the host cell is *Escherichia coli*.

8. The host cell of claim 7, wherein a C-terminal ω-fragment of a β-galactosidase of the *Escherichia coli* is encoded.

9. A method of preparing the vector of claim 3, comprising the following steps:

(1) performing PCR with a set of primers for mutating a nucleic acid sequence between the –35 region and the –10 region of a β-galactosidase promoter in a promoter region of a β-galactosidase to comprise at least one recognition site for an endonuclease, and using an original vector comprising an original β-galactosidase promoter and a reporter gene regulated by the original β-galactosidase promoter as a template for PCR amplification, to obtain a PCR amplification product with the promoter of claim 1; and (2) cyclizing the PCR amplification product obtained using the primers in step (1) by recombination to obtain a vector.

10. The method of claim 9, wherein nucleic acid sequences of the set of primers in step (1) are SEQ ID NO: 17 and SEQ ID NO: 18.

11. A kit, comprising either a vector comprising the promoter of claim 1 or an isolated host cell comprising the vector.

12. The method of claim 9, wherein before step (1), the method further comprises performing codon optimization on the reporter gene.

13. The method of claim 9, wherein the reporter gene is a lacZ gene whose nucleic acid sequence is SEQ ID NO: 39.

14. The vector of claim 3, wherein the reporter gene is a lacZ gene whose nucleic acid sequence is SEQ ID NO: 39.

15. The method of claim 9, wherein the reporter gene is a lacZ gene encoding an N-terminal α-fragment of the β-galactosidase.

16. The promoter of claim 1, wherein the −10 region has a nucleic acid sequence of 5'-TATGTT-3'.

17. The vector of claim 4, wherein the foreign DNA is at least 24 base pairs in length.

18. A method of using the vector of claim 3, comprising the following steps:
   (1) linearizing the vector by digesting the at least one recognition site for the endonuclease in the mutated nucleic acid sequence between the −35 region and the −10 region of the promoter to obtain a linearized vector; and
   (2) ligating a foreign DNA into the linearized vector of step (1), thereby obtaining a vector comprising a foreign DNA inserted into the mutated nucleic acid sequence between the −35 region and the −10 region of the promoter.

19. The method of claim 18, wherein the linearizing in step (1) is performed through endonuclease digestion and PCR amplification.

20. The method of claim 18, wherein digesting is performed with an appropriate endonuclease selected from the group consisting of EcoRV, AleI, BamHI, XhoI, and PmlI.

* * * * *